US006533795B1

(12) United States Patent
Tran et al.

(10) Patent No.: US 6,533,795 B1
(45) Date of Patent: Mar. 18, 2003

(54) DUAL FUNCTION SUTURING APPARATUS AND METHOD

(75) Inventors: Minh Tran, Fountain Valley, CA (US); George White, Corona, CA (US)

(73) Assignee: Opus Medical, Inc, San Juan Capistrano, CA (US)

( * ) Notice: Subject to any disclaimer, the term of this patent is extended or adjusted under 35 U.S.C. 154(b) by 0 days.

(21) Appl. No.: 09/547,171

(22) Filed: Apr. 11, 2000

(51) Int. Cl.$^7$ .............................................. A61B 17/04
(52) U.S. Cl. ...................................................... 606/144
(58) Field of Search ......................................... 606/144

(56) References Cited

U.S. PATENT DOCUMENTS

| 3,946,740 A | | 3/1976 | Bassett | |
|---|---|---|---|---|
| 4,164,225 A | | 8/1979 | Johnson | 606/146 |
| 4,621,640 A | | 11/1986 | Mulhollan et al. | |
| 4,836,205 A | | 6/1989 | Barrett | |
| 4,923,461 A | | 5/1990 | Caspari et al. | 606/146 |
| 4,935,027 A | | 6/1990 | Yoon | |
| 4,957,498 A | | 9/1990 | Caspari et al. | 606/146 |
| 5,397,325 A | * | 3/1995 | Della Badia et al. | 112/169 |
| 5,445,167 A | | 8/1995 | Yoon et al. | 606/143 |
| 5,609,597 A | | 3/1997 | Lehrer | 606/139 |
| 5,645,552 A | | 7/1997 | Sherts | 606/143 |
| 5,665,108 A | | 9/1997 | Galindo | |
| 5,741,281 A | | 4/1998 | Martin | |
| 5,776,150 A | | 7/1998 | Nolan et al. | |
| 5,792,152 A | | 8/1998 | Klein et al. | |
| 5,797,927 A | * | 8/1998 | Yoon | 606/139 |
| 5,984,933 A | | 11/1999 | Yoon | |
| 6,001,109 A | | 12/1999 | Kontos | |
| 6,048,351 A | | 4/2000 | Gordon et al. | 606/144 |
| 6,051,006 A | * | 4/2000 | Shluzas et al. | 606/144 |

* cited by examiner

*Primary Examiner*—Gary Jackson
(74) *Attorney, Agent, or Firm*—Stout, Uxa, Buyan & Mullins, LLP; Donald E. Stout

(57) ABSTRACT

A suturing instrument and method for placing mattress stitches in soft tissues is described. An elongate shaft with a stationary jaw and a moveable jaw disposed at the distal end is coupled to a handle grip at the proximal end configured to manipulate the jaws into open and closed positions. The jaws are configured to allow for atraumatic grasping of soft tissues. The stationary jaw is comprised of a serrated face incorporating apertures through which needles attached to opposite ends of a single strand of suture material may be driven out into and through grasped tissue. The serrated upper jaw is configured with needle catch adapted to accept and capture the needles and suture. The handle is released to open the moveable jaw, the instrument may be withdrawn, trailing the suture, and leaving a mattress stitch in the grasped tissue.

60 Claims, 19 Drawing Sheets

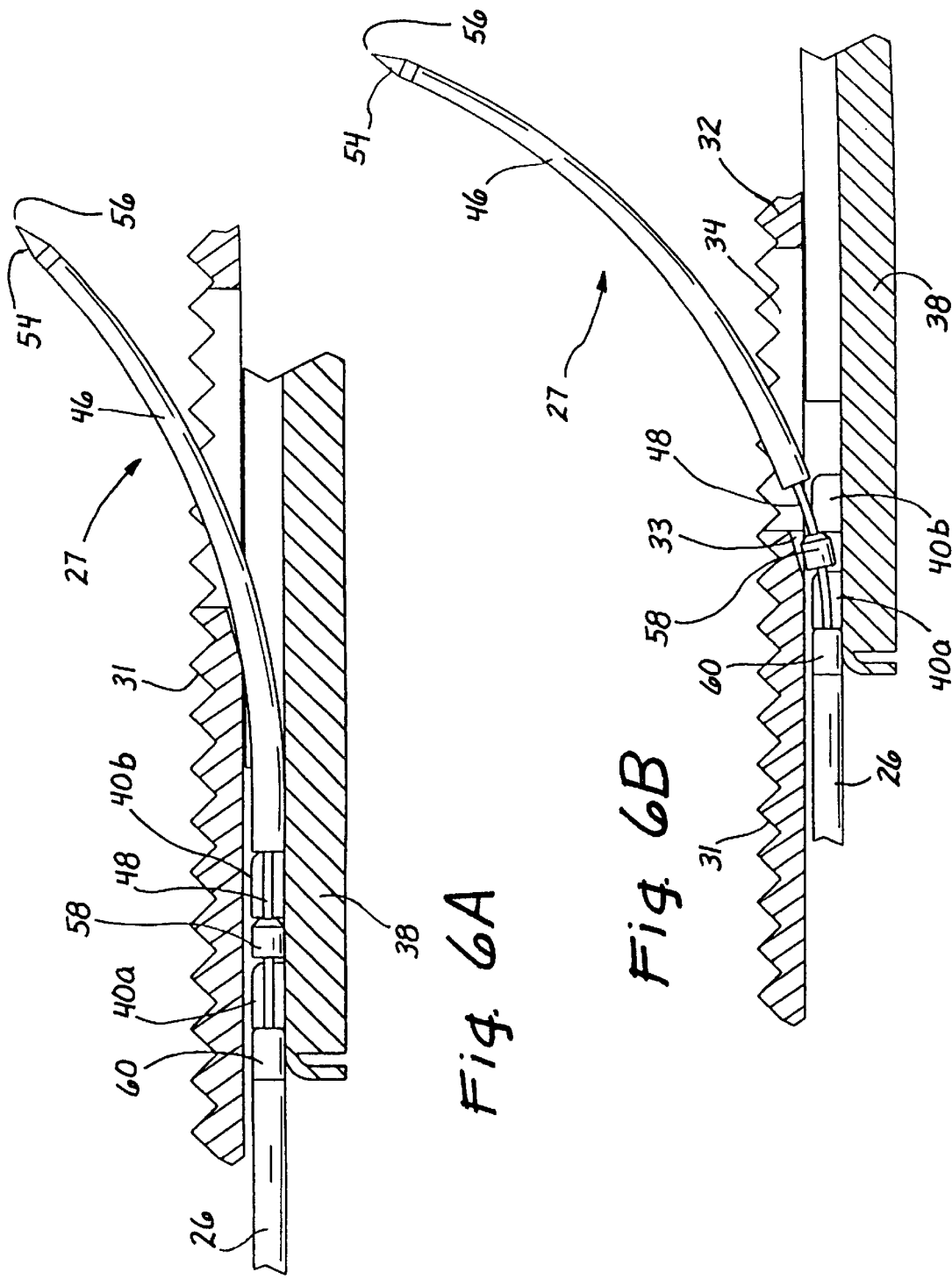

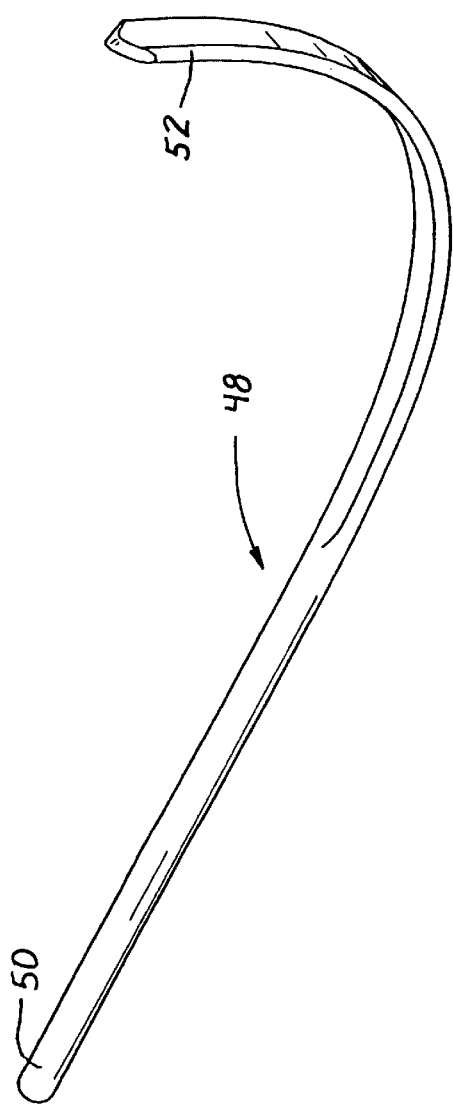
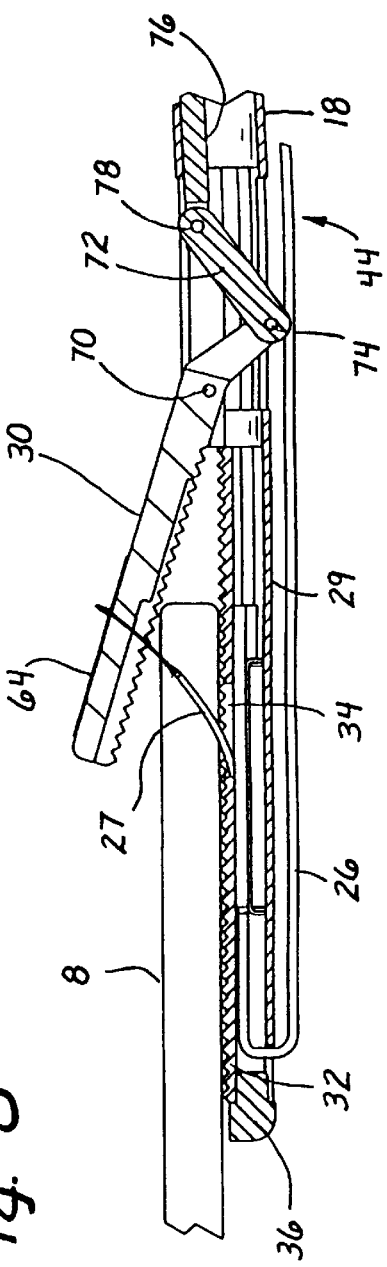

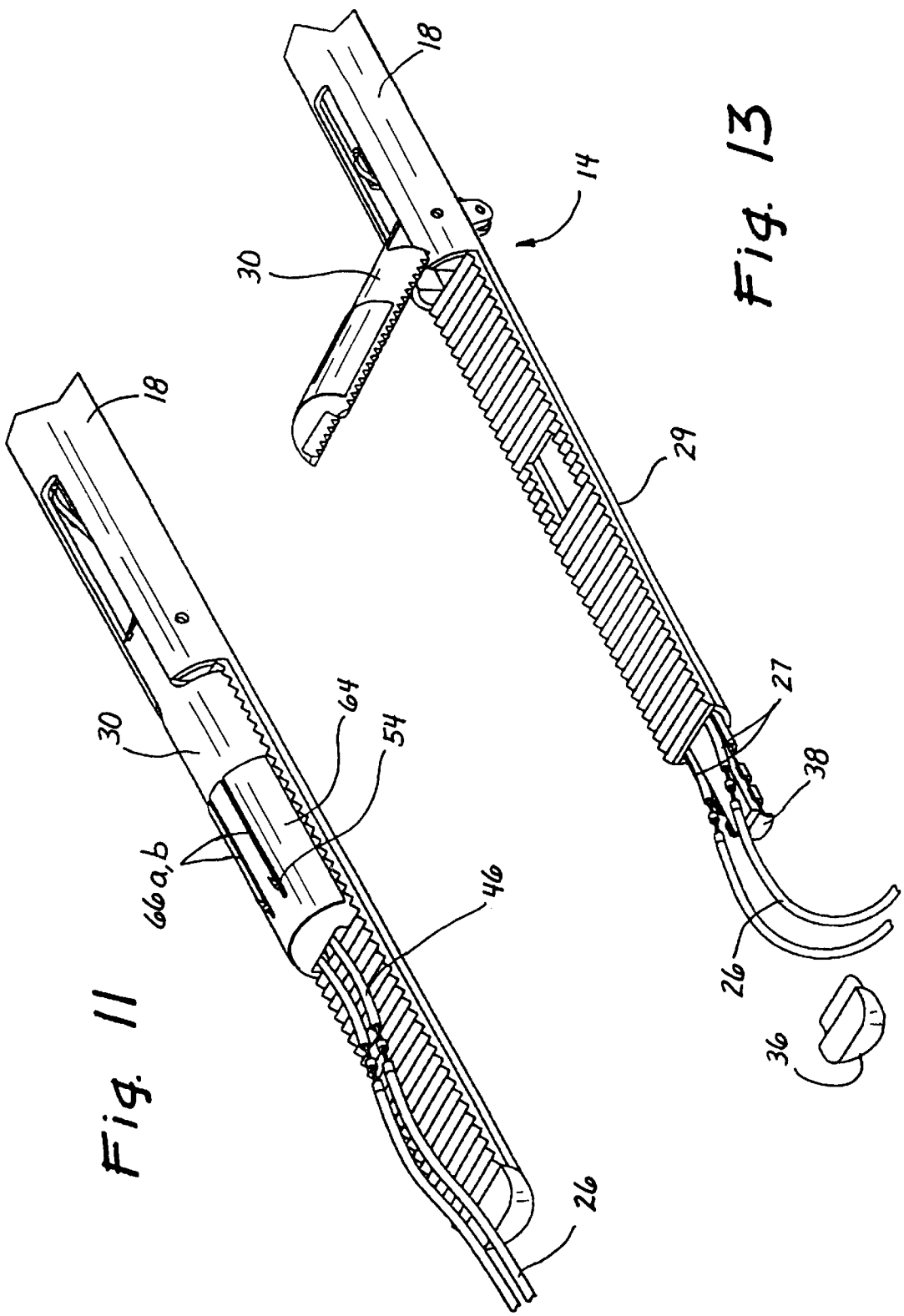

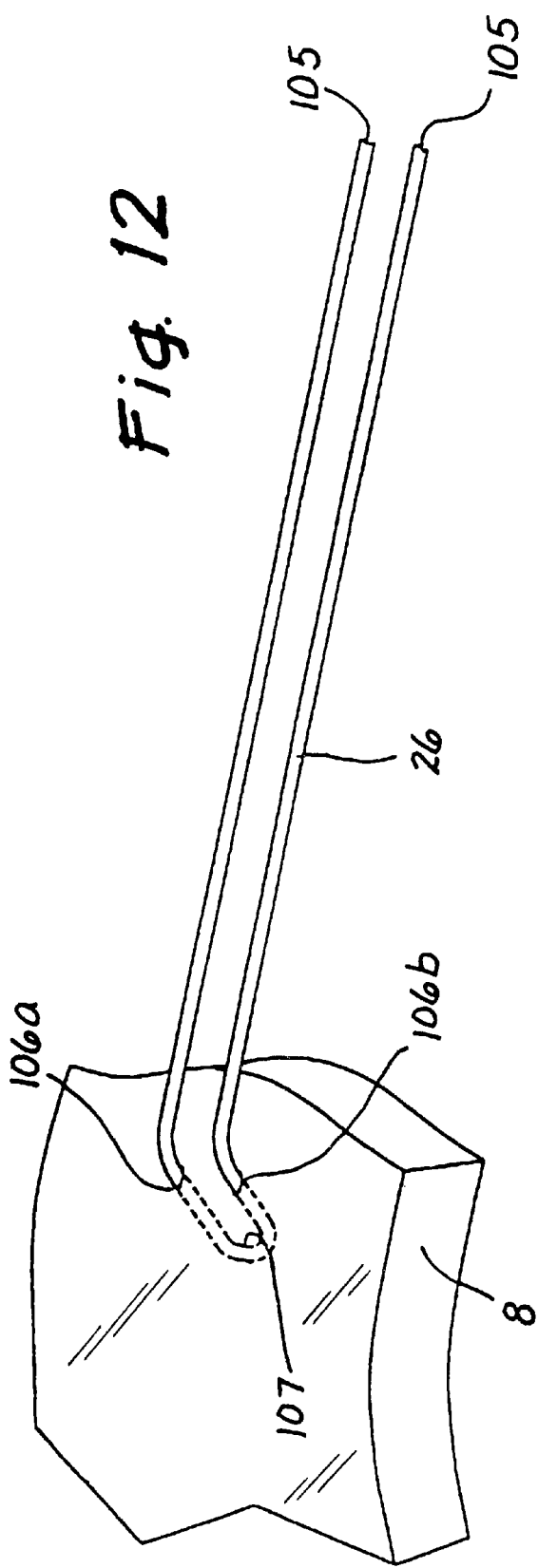

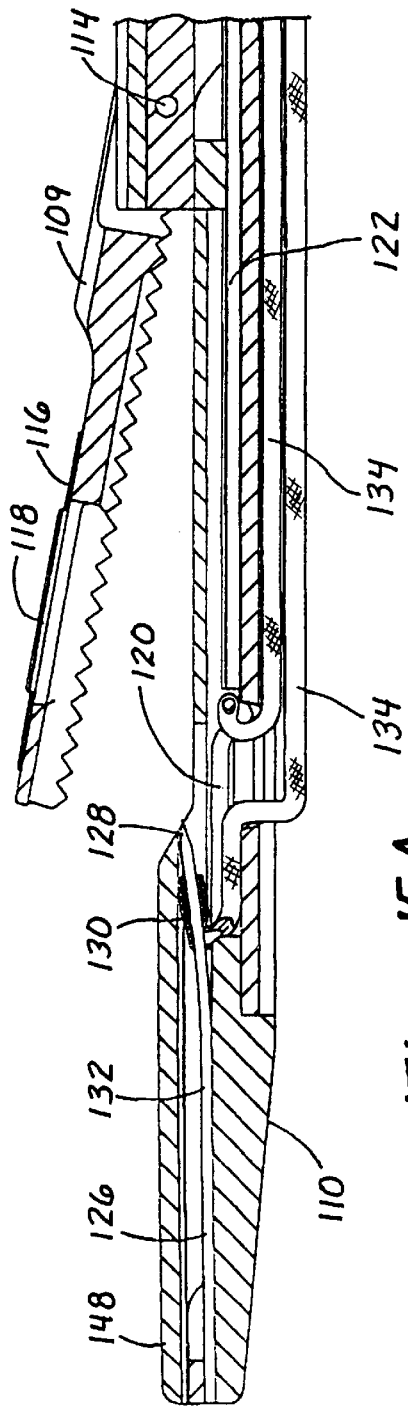
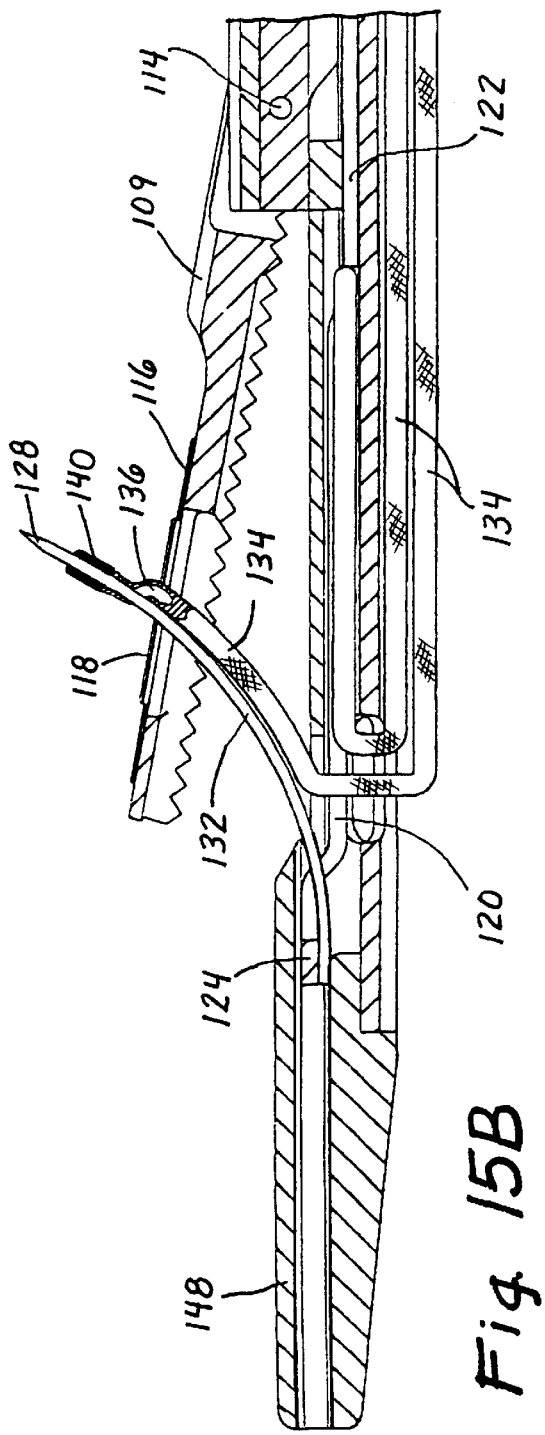
Fig. 15A
Fig. 15B

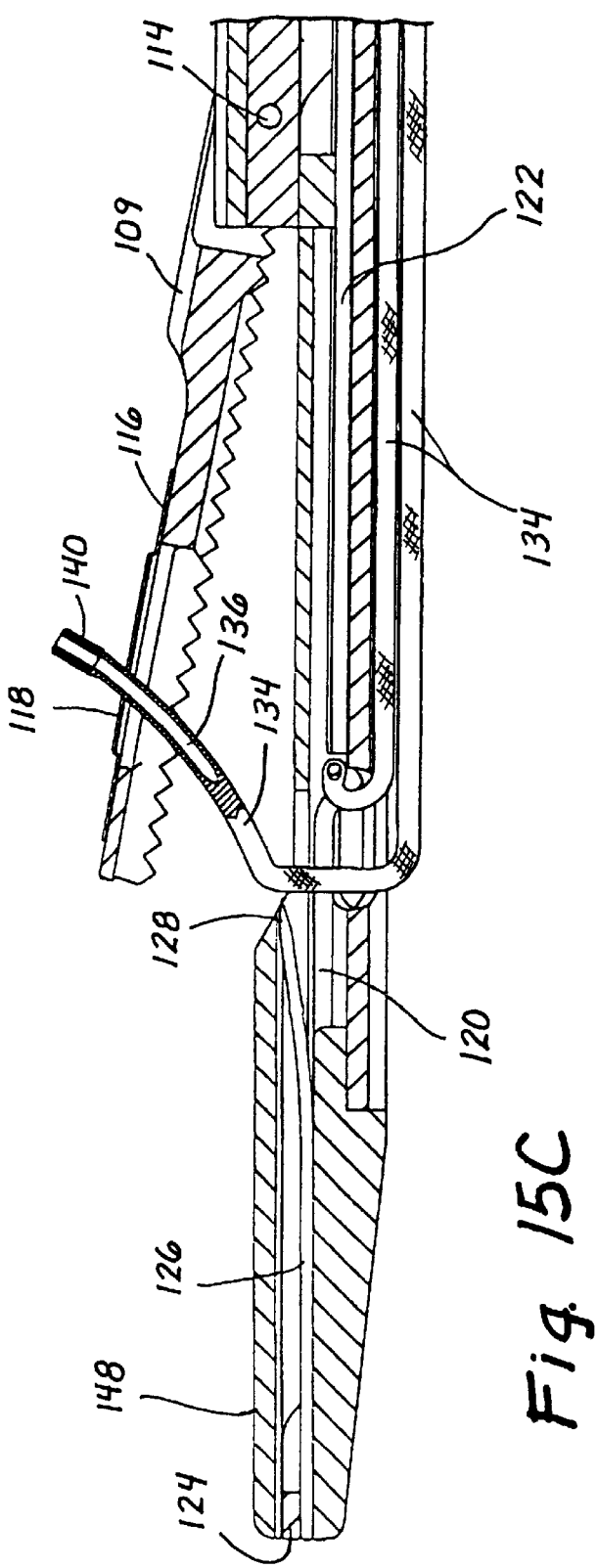
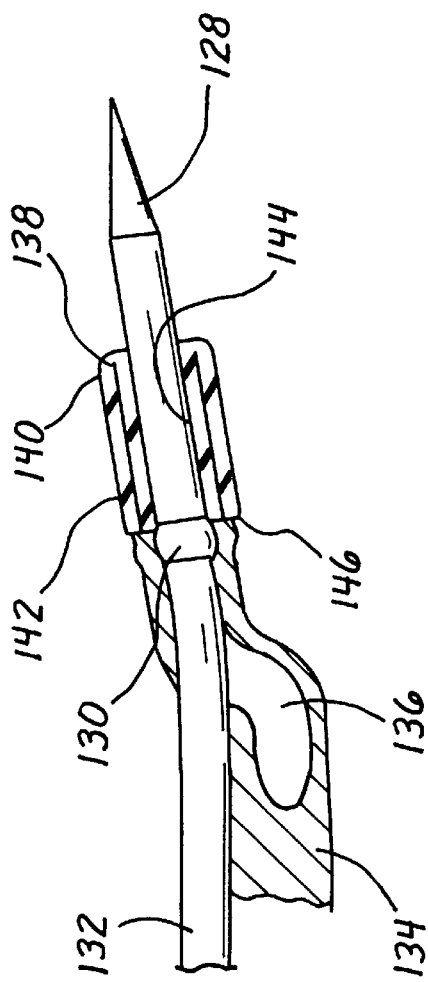
Fig. 15C
Fig. 16

DUAL FUNCTION SUTURING APPARATUS AND METHOD

This application is related to co-pending application Ser. No. 09/475,495, filed on Dec. 30, 1999, and entitled Method and Apparatus for Attaching Connective Tissues to Bone Using a Knotless Suture Anchoring Device, and to co-pending application Ser. No. 09/515,360, filed on Feb. 29, 2000, and entitled Single-Tailed Suturing Method and Apparatus, both of which are herein expressly incorporated by reference.

BACKGROUND OF THE INVENTION

The present invention relates to a method and apparatus for placing sutures in tissue, and more particularly to a method and device for arthroscopic repair of a torn rotator cuff.

Suturing of body tissues is a time consuming aspect of most surgical procedures. Many surgical procedures are currently being performed where it is necessary to make a large opening to expose an area of the body that requires surgical repair. Endoscopes are available for viewing certain interior regions of the body through a small puncture wound without exposing the entire body cavity. These instruments can be used in conjunction with specialized surgical instrumentation to detect, diagnose, and repair areas of the body that were previously only able to be repaired using traditional "open" surgery.

In the past, there have been many attempts to simplify the surgeon's task of driving a needle carrying suture material through body tissues to approximate, ligate and fixate them. Many prior disclosures, such as described in U.S. Pat. No. 919,138, to Drake et al., issued Apr. 20, 1909, employ a hollow needle driven through the tissue with the suture material passing through the hollow center lumen. The needle is withdrawn leaving the suture material in place, and the suture is tied, completing the approximation. A limitation of these types of devices is that they are particularly adapted for use in open surgical procedures where there is room for the surgeon to manipulate the instrument.

Others have attempted to devise suturing instruments that resemble traditional forceps, such as U.S. Pat. No. 3,946,740 to Bassett, issued Mar. 30, 1976. These devices pinch tissue between opposing jaws and pass a needle from one jaw through the tissue to the other jaw, where grasping means pull the needle and suture material through the tissue. A limitation of these designs is that they also are adapted primarily for open surgery, in that they require exposure of the tissues to be sutured in order that the tissue may be grasped or pinched between the jaws of the instrument. This is a severe limitation in the case of endoscopic surgery.

The term "endosurgery" means endoscopic surgery or surgery performed using an endoscope. In conjunction with a video monitor, the endoscope functions as the surgeon's surrogate eyes for the purpose of performing the surgical procedure. Operations using an endoscope are significantly less invasive when compared to traditional open surgery. Patients usually return home the next day or in some cases, the same day of the endosurgical procedure. This is in contrast to standard open surgical procedures where a large incision divides the muscle layers and allows the surgeon to directly visualize the operative area. Patients may stay in the hospital for 5 to 6 days or longer following open surgery. In addition, after endosurgical procedures, patients often return to work within a few days versus the traditional 3 to 4 weeks recuperative period following open surgery.

Access to the operative site using endosurgical or minimally invasive techniques is accomplished by inserting small tubes called trocars into a body cavity. These tubes have a diameter of, for example, between 3 mm and 30 mm and a length of about 150 mm (6 inches). There have been attempts to devise instruments and methods for suturing within a body cavity through these trocar tubes.

Such an instrument is disclosed in U.S. Pat. No. 4,621,640 to Mulhollan et al., issued Nov. 10, 1986. Mulhollan et al. describe an instrument that may be used to hold and drive a needle, but make no provision for retrieval of the needle from the body cavity, nor the completion of the suture by tying. The instrument disclosed in the Mulhollan et al. patent is limited, in that the arc through which the needle must be driven is perpendicular to the axis of the device.

Another such instrument intended for endoscopic use is described by U.S. Pat. No. 4,935,027 to Yoon, issued Jun. 19, 1990. This instrument uses oppositional hollow needles or tracks pushed through the tissue and co-apted to create a tract through which the suture material is pushed. It is not clear from the disclosure how these curved tracks would be adapted to both be able to pierce the tissue planes illustrated, parallel to the tips of the tracks, and be curved toward each other to form the hollow tract.

Yet another instrument and method is shown in U.S. Pat. No. 4,923,461 issued May 8, 1990 and U.S. Pat. No. 4,957,498 issued Sep. 18, 1990, both to Caspari. Caspari discloses an endoscopic instrument suitable for use through a trocar, that resembles the Yoon approach, but with a single hollow needle on one of a set of oppositional jaws. The jaws simultaneously close, grasping the tissue. The jaw opposite the hollow needle has a window through which the hollow needle passes as the jaws close, freeing the lumen of the hollow needle from the tissue. Much like the Yoon patent, a suture or suture snare is pushed down through the lumen and retrieved from the suture site, the jaws released, and the suture pulled back out through the trocar. This device may be used to place simple stitches in tissues that have been mobilized and have an edge accessible to the jaws. A limitation of the device is the manipulation that must be done with the snare if a suture other than a monofilament is used.

Another instrument specifically adapted for the repair of a torn anterior cruciate ligament or for meniscal repair is disclosed in U.S. Pat. No. 4,836,205 to Barrett. The Barrett patent combines in a single instrument the functions of grasping the tissue to be sutured and the passing of the needles through that tissue. It is to be understood that this instrument is designed for use specifically under endoscopic view, and through trocars as previously described. A fairly generic endoscopic grasper is disclosed that has been adapted to allow for a hollow lumen from the handle of the grasper down to the distal tip of the grasper jaws. An elongate needle of 8 to 10 inches in length may be passed through this hollow lumen. The needle, being significantly longer than the grasper, is introduced through the handle of the grasper, and may be driven through the tissue being held in the grasping jaws of the device. The needle is then retrieved from the tissue via a trocar port placed substantially opposite the port through which the grasper is introduced. If a mattress stitch is desired, two needles attached to opposite ends of a suture are both passed through the tissue and retrieved. A limitation of this device is that there must be both visual and physical access to both sides of the tissue flap to be sutured. This requires trocars to be placed opposite each other and roughly on a line intercepting the tissue. This is a severe limitation in the instance of shoulder repair, and specifically in repair of the rotator cuff.

There have been other attempts to improve the methods of tissue repair. These include the development of staplers and anchoring devices. In response to some of the aforementioned problems in placing sutures in tissues endoscopically, manufacturers have developed tissue staplers. These devices utilize stainless steel or titanium staples that are constructed much like the staples used to hold papers together. The major disadvantage of these kinds of staplers is that they leave metal in the body. For some tissues this is not a problem, however in some procedures, metal staples left within the tissues can be a major hindrance to the healing process.

In orthopedic surgery, many different designs for bone anchors have been developed. These anchors allow soft tissues to be reattached to bone, and simplify the process by removing the need to create a trans-osseous tunnel. Trans-osseous tunnels are created in bones to allow suture material to be threaded through and tied across the bony bridge created by tunnels after it has been placed through the soft tissues and tied with conventional knots. Anchors fabricated from stainless steel or titanium are commonly used in joint reconstructions, and because the metal is contained in the bone, it does not typically cause a problem with healing.

While endoscopy has certainly found favor with many physicians as an alternative operative modality, the advanced skill set and operative time necessary to become an efficient and practiced endoscopist have proven to be a challenge for a large portion of the surgical community. The cost pressures brought about by large scale patient management (the continued rise and success of health maintenance organizations or HMO's) have also caused the surgical community to carefully evaluate the overall costs and long-term outcomes of some of the procedures that have been tried via an endoscopic approach. While the laparoscopic cholecystectomy (gall bladder removal) has well proven its worth in the past 8–10 years, many other procedures have not shown similar cost effectiveness and positive long-term outcomes.

Hence, alternatives have been sought to bridge the gap between skill and equipment intensive endoscopic surgery and more familiar open surgery. As such, under the broad umbrella of "minimally invasive surgery" which would include endoscopic surgery, a relatively new approach called "mini-incision surgery" has begun to emerge. This approach uses the principles of traditional open surgery, along with some of the equipment advances of endoscopy in an attempt to provide the patient with the best of both worlds.

Perhaps the most visible of these new approaches is the emergence of minimally invasive heart surgery, both for coronary bypass and for valve replacement. Techniques and tools for cardiovascular surgery have begun to be used that allow the heart surgeon to perform procedures through small incisions between the ribs that previously required a massive incision and splitting of the sternum to gain access to the heart.

In a similar way, orthopedic surgeons have begun to explore alternatives to the traditional open approach for the many indications requiring reconstruction of some aspect of the shoulder. As they did in adopting minimally invasive approaches to knee repair and re-construction, the use of either an endoscope or a "mini-open" approach is gaining in popularity with surgeons, patients and third party payers.

It is an increasingly common problem for tendons and other soft, connective tissues to tear or to detach from associated bone. One such type of tear or detachment is a "rotator cuff" tear, causing pain and loss of ability to elevate and externally rotate the arm. Complete separation can occur if the shoulder is subjected to gross trauma, but typically, the tear begins as a small lesion, especially in older patients.

The rotator cuff of a shoulder joint is made up of a combination of the distal tendinous portion of four muscles, supraspinatus and subspinatus, subscapularis and teres minor. The cuff is attached to the upper, anterior and posterior faces of the trochiter by covering the upper pole of the humeral head. Proper functioning of the tendinous cuff, 3 to 4 millimeters thick, depends on the fundamental centering and stabilizing role of the humeral head with respect to sliding action during anterior and lateral lifting and rotation movements of the arm.

The musculotendinous cuff passes under an osteofibrous arch, which is made up from the front to the rear by a portion of the acromion, the coracoacromial ligament and the coracoid process, thereby forming a canal. A sliding bursa passes between the musculotendinous cuff and the walls of the osteofibrous arch. Therefore, there is a potential and sometimes detrimental interaction between the musculotendinous cuff and the acromiocoracoidian arch, particularly during lateral and anterior lifting movements of the arm. The repeated rubbing of the cuff against the walls of the osteofibrous arch results in wearing of the tendinous cuff by progressive abrasion. The rubbing can be increased, inasmuch as arthosis lesions with severe osteophytes may thicken the walls of the aforementioned arch, becoming more aggressive as the cuff gets older.

With time, gradual thinning is brought about, often resulting in a trophic perforation (less than 1 $cm^2$) of the cuff, particularly in the hypo-vascularized and fragile area where the supraspinatus muscle is joined. A fall may provide a more extensive rupture by disjunction of the supraspinatus muscle, with extension towards the front (subscapularis muscle) or the rear (subspinatus muscle). The degenerative rupture of the rotator or musculotendinous cuff may be of a varied size:

grade 1—perforation (less than 1 $cm^2$) reaching the supraspinatus muscle;

grade 2—supraspinatus rupture (greater than 1 $cm^2$);

grade 3—massive rupture concerning the supraspinatus, subspinatus, subscapularis muscles and sometimes the teres minor muscle.

It is possible to carry out surgery to reconstruct the rotator cuff. This is done by re-covering the humeral head, giving back to the cuff its capturing and stabilizing role and re-establishing a harmonious scapulohumeral rhythm. Reconstruction requires excision of the coracoacromial ligament and cleaning of the subacromial space, including suppression of the arthrosis legions and thinning of the anterior portion of the acromion.

The typical course for repair of a tom rotator cuff today is to do so through an open incision. This approach is presently taken in almost 99% of rotator cuff repair cases. Two types of open surgical approaches are employed for repair of the rotator cuff, one known as the "classic open" and the other as the "mini-open". The classic open approach requires a large incision of 6 to 9 centimeters (cm) and complete detachment of the deltoid muscle from the acromion to facilitate exposure. Following the suturing of the rotator cuff to the humeral head, the detached deltoid is surgically reattached. Because of this maneuver, the deltoid requires postoperative protection, thus retarding rehabilitation and possibly resulting in residual weakness. Complete rehabilitation takes approximately 9 to 12 months.

The mini-open technique, which represents the current growing trend and the majority of all surgical repair procedures, differs from the classic approach by gaining access through a smaller incision of 3 to 5 cm and splitting rather than detaching the deltoid. Additionally, this procedure is typically used in conjunction with arthroscopic acromial decompression. Once the deltoid is split, it is retracted to expose the rotator cuff tear. The cuff is debrided and trimmed to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as trans-osseous tunnels, are "punched" through the bone laterally from the abraded or notched surface to a point on the outside surface of the greater tuberosity, commonly a distance of 2 to 3 cm.

There are a few different methods for placing the suture material in the supraspinatus tendon. Because one of the most common failure modes for rotator cuff repair lies in the sutures pulling out of the soft tissue, much care is taken to place the sutures such that the most security possible is achieved. This is typically done by using either a mattress stitch or a more complex stitch called a "modified Mason-Allen". The goal of both of these stitches is to spread the forces imparted by the sutures on the tissues by involving a pledget of tissue between the entry and exit points of the suture ends. The mattress stitch incorporates essentially a "down, over and back up" path for the suture.

Finally, the cuff is secured to the bone by pulling the suture ends through the trans-osseous tunnels and tying them together using the bone between two successive tunnels as a bridge, after which the deltoid muscle must be surgically reattached to the acromion.

Although the above described surgical technique is the current standard of care for rotator cuff repair, it is associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally using instruments and techniques such as the Caspari punch previously described. This creates a simple stitch instead of the more desirable mattress or Mason-Allen stitch. Rather than thread the suture through trans-osseous tunnels which are difficult or impossible to create arthroscopically using current techniques, an anchor is driven into bone at a location appropriate for repair. The repair is completed by tying the cuff down against bone using the anchor and suture.

Early results of less invasive techniques are encouraging, with a substantial reduction in both patient recovery time and discomfort. However, as mentioned, this approach places only one loop of suture in the cuff for each anchor, reducing the fundamental strength of the repair. The knots in the tendon can be bulky and create a painful impingement of the tendon on the bone. This is because the knots end up on top of the cuff, in the sub-acromial space, and have the opportunity to rub on the acromion as the arm is raised. Because non-absorbable suture materials are used for these types of repairs, the suture and associated knots are not absorbed into the body, and hence provide a constant, painful reminder of their presence.

None of the prior art devices are adaptable to effect the placement of a mattress stitch in grasped tissues, nor are they adaptable to place sutures precisely and controllably while making provision for needle retrieval when using endoscopic techniques. None of the prior art devices make it possible to place a mattress stitch into, for example, the supraspinatus tendon utilizing an endoscopic approach.

Accordingly, it would be desirable to provide a family of novel suturing devices that overcomes the above set out disadvantages of prior known devices in a simple and economical manner. In particular, a system which would be capable of creating a mattress stitch in the tendon, using endoscopic techniques, to increase the soft tissue pullout strength would be advantageous, as would a system that does not require the traditional knots to secure the suture to the tendon.

SUMMARY OF THE INVENTION

Accordingly, a new and novel approach to securing a mattress stitch in a tissue flap has been developed. An instrument that combines the function of both grasping the tissue and passing sutures through the tissue to form a mattress stitch, in an endoscopic environment, is herein described.

In the method of the present invention the instrument is inserted through a portal known as a trocar cannula. The portal is created by first making an incision in the skin and then inserting a cannula through the incision to the repair site. The distal end of the instrument is inserted through the cannula under direct visualization from a second trocar cannula that has been previously inserted. The visualization is accomplished via an endoscope, which is well known in the art. The instrument is inserted until the jaws reach, for example, torn rotator cuff tissue. In operation, the distal end of the grasper aspect of the instrument is positioned at the repair site against the tissue to be grasped. The moveable jaw is pivoted toward the stationary jaw by squeezing the handle lever. As the handle lever moves inwardly by pivoting about a pivot pin, a cable attached to the top of the handle lever is drawn rearwardly, proximal of the handle. When the cable is drawn rearwardly, the movable jaw pivots towards the stationary jaw to close the jaws. Once the appropriate section of tissue is isolated and grasped by the jaws, the lever may be locked in its closed position using a latch mechanism.

Once the surgeon is satisfied with the placement of the grasper on the grasped tissue, the surgeon can then deploy the suture needles to create a mattress stitch in the tissues, for example, a torn rotator cuff. In operation, the suture needles may be advanced through the grasped tissues by pulling on a trigger. The trigger is attached to a slide cable, and pulling on the trigger draws the slide cable rearwardly towards the proximal end of the instrument, pulling against the force of a return spring. In turn, the slide cable pulls a needle carriage with suture needles releasably held in the carriage. The needle carriage resides within the lower stationary jaw of the instrument, and at the urging of the trigger via the slide cable, is able to move from distal to proximal locations within the jaw. As the carriage moves proximally, the tips of the suture needles begin to clear the distal edge of an aperture created in the lower stationary jaw and begin to penetrate through the underside of the grasped tissue and advance upwardly towards the movable jaw.

In one preferred embodiment, the needle carriage is coupled to the needles by a set of tabs that engage shoulders on the needles. The shoulders of the needles are formed by the proximal end of the needle holding the suture, and an outer sleeve that is slidably disposed about a flexible inner ribbon affixed to the proximal end. The ribbon has attached to its distal end a needle tip which limits the distal travel of the outer sleeve and creates the second shoulder at the proximal end of the outer sleeve.

In the aforementioned embodiment, the moveable jaw incorporates a passive needle catch. The jaw is constructed with a window in the face of the jaw to allow the needles to penetrate through to a passive catch that incorporates a thin stainless steel membrane with slots configured to capture the tips of the needles. As the suture needles approach the end of the ejection stroke, the distal ends of the needles pass through the upper movable jaw and the capture member. As the needles pass through the upper jaw they begin to separate from the needle carriage. The proximal end of the needles' curved outer sleeve separates from the first tab on the needle carriage, in such a manner that there is no further force pushing on the sleeve to force it through the tissues. The force now pushing on the suture needles is concentrated on the proximal end of the needles. As the needle carriage is advanced further, the needles' curved outer sleeves stay stationary due to the resistance caused by their contact with the tissues. However, the flexible inner ribbon of each needle is free to advance further. The gap between the needles' curved outer sleeves and the proximal end of each needle begins to close until there is no gap at all. At this point the penetrating tip of each needle has extended beyond the distal end of the needle's curved outer sleeve, exposing the flexible inner ribbon. Once the gap is closed between the proximal end of the needle and the outer sleeve, the needle assembly will again continue to advance as one unit through the grasped tissues. As the needle carriage advances further, it pushes on the needle assembly until each needle has been pushed beyond the point of contact with the needle carriage. At this point the suture needles are through the grasped tissues and protruding through the upper movable jaw and into the needle catch. Due to a pre-defined curve in the flexible inner ribbon, the penetrating tip remains extended from the distal end of each needle's curved outer sleeve.

At this point, any pull force being applied by the grasper on the grasped tissues is relaxed. Once the tissue is in a relaxed state, the jaws of the grasper are then opened. The handle lever is unlocked from the locking mechanism and returns to an open position due to the pull force exerted on it by means of a return spring. As the return spring pulls on the lever, it pivots about a pin. As handle lever pivots, it pulls on the jaw cable coupled to the handle lever by means of a pin. This advances the jaw cable towards the distal end of the barrel. As the jaw cable advances, it pushes on a linkage which then pushes on the movable upper jaw, causing the upper jaw to pivot about a pin. This pivoting motion causes the moveable jaw to open and separate away from the stationary jaw. As the movable upper jaw begins to open, the suture needles for the most part remain stationary due to resistance caused by their contact with the tissues through which they have been driven. At a point just beyond the distal end of the suture needle's curved outer sleeve, the needle catch on the upper jaw will trap the suture needles at a point between the curved outer sleeve and the penetrating tip, grasping the flexible inner ribbon and securing the needles by interference with the shoulder created between the inner ribbon and the penetrating tip.

As the upper jaw slips past the needle's outer sleeve, the small slit in the needle catch closes down around the needle's ribbon. The slit is large enough so as not to restrict the movement of the ribbon, but is too small to allow the penetrating tip to pass back through. This is because the needle catch on the upper jaw can only be deflected in an outward direction, away from the outer surface of the upper jaw. Since the distal end of the suture needles are trapped in the needle catch on the upper jaw, they are pulled through the tissues as the upper jaw is opened further.

When the jaws of the grasper are fully extended, the suture needles are nearly pulled through the tissue. To complete the pullout of the suture needles, it is necessary to pull on the grasper, and begin to remove it from the repair site. Once the suture needles are through the tissue, they can be secured by closing down the jaws of the grasper. After closing the grasper jaws, the instrument can be retracted back through the portal via the trocar cannula.

As the instrument is removed from the suture site, the free ends of the suture are retrieved as well. This causes the suture to pass through the tissues at the puncture sites. As the suture is pulled through, the loop end of the suture is pulled snug against the underside of the tissues to form what is referred to as a mattress stitch. This process may be repeated as necessary, depending on the number of sutures required for the particular procedure being undertaken.

The instrument may be reloaded with new suture needles by removing an end cap covering the distal end of the lower stationary jaw. After the end cap is removed, the needle carriage may be advanced beyond the distal end of the lower jaw to be reloaded. To advance the needle carriage in this manner simply requires advancing the handle trigger towards the distal end of the grasper. Once new suture needles are reloaded, end cap may be replaced. The excess suture loop that will form the next stitch passes through the lower stationary jaw through a small notch. This extra length of suture is left outside the body as the grasper is inserted back through the portal to the repair site as previously described.

Another embodiment of the grasper/suturing device modifies the needle and suture interface. Instead of the needle carrying the suture by an attachment point at the distal end of the needle, this embodiment releasably attaches the suture to the needle at nearly the proximal end. The major elements of the above described instrument remain the same; i.e. the grasper function with a lower fixed jaw and an upper moveable jaw, and a needle carriage coupled to a trigger for actuation of the stitching function.

However, in this second embodiment, the needles are non-releasably attached to the needle carriage; that is to say that they are permanently attached to the carriage. The suture, which is of a braided configuration that is known in the art and has a hollow core, is configured to have a ferrule attached to its ends. This ferrule is constructed such that the hollow braided suture is crimped or otherwise mechanically or adhesively attached to the ferrule. The ferrule includes an interior lumen which is dimensioned such that it is able to be slidably disposed over the end of the needles which are attached to the needle carriage. The needles are configured to have a step, preferably a radiused step, that functions as a stop for the ferrule over which the interior lumen may not pass.

Both ends of the suture are loaded onto individual needles, with the excess suture between the ends contained within the bounds of the device. Functionally, as the aforementioned driver trigger is pulled by the surgeon, the needles are disposed to exit from the window in the stationary lower jaw and to transit a curved path through the grasped tissues until reaching a suture catch disposed upon the upper surface of the moveable upper jaw. The needles, carrying the ferrule and attached suture, pass through the suture catch. Since the ferrule is slidably disposed upon the needle, as the trigger is released, the needle carriage withdraws and the needles attached to the carriage are withdrawn through the tissue, leaving the ferrule and attached suture deposited within the suture catch.

As described previously, the tension on the grasper is released, and the instrument is withdrawn from the operative trocar, trailing the suture behind, and creating a mattress stitch in the grasped tissues.

Now it may be seen by those skilled in the art, the combination of grasping tissues to be sutured and precisely placing a mattress stitch in the grasped tissues while working through a trocar port effects a significant advance in the art. It is therefore an object of the present invention to provide an endoscopic instrument adapted for the grasping of tissues and creating a mattress stitch within those tissues.

It is a further object to provide an instrument that allows for the reloading of additional sutures and suture needles for placement of subsequent stitches.

The invention, together with additional features and advantages thereof, may best be understood by reference to the following description taken in conjunction with the accompanying illustrative drawing.

BRIEF DESCRIPTION OF THE DRAWINGS

FIGS. 6A through 6D are sequential cross-sectional views illustrating certain steps of an inventive method for deploying suture needles through grasped tissue, using an embodiment of the apparatus of the present invention;

FIG. 7 is a perspective view of the internal needle ribbon of the present invention;

FIG. 8 is a side, partial cross-sectional view of the jaws of the apparatus of the present invention, clamping down on a portion of a patient's rotator cuff;

FIG. 11 is an enlarged perspective view of the jaws of the present invention, wherein suturing material has been grasped therein;

FIG. 12 is a schematic perspective view illustrating a mattress stitch which remains in a portion of the rotator cuff of a patient after a suturing procedure has been completed in accordance with the principles of the present invention;

FIG. 13 is an enlarged perspective view of the jaws of the present invention, illustrating the reloading of the suture needles;

FIGS. 15A through 15C are detail cross-sectional views, in sequence, illustrating constructional details and a method for using the alternate embodiment shown in FIG. 14;

FIG. 16 is an enlarged detail view, in cross-section, of the tip of the needle illustrated in FIGS. 14 through 15C.

DESCRIPTION OF THE PREFERRED EMBODIMENT

The present invention relates to a method and apparatus for the arthroscopic repair of torn tissue and bone at a surgical repair site using a device, which is a combination tissue grasper and suture placement device. Although the present invention is described primarily in conjunction with the repair of a torn rotator cuff, the apparatus and method could also be used in arthroscopic repair at other sites, such as the knee, elbow, or hip, for example, as well as in conjunction with other surgical techniques.

Figure 1:
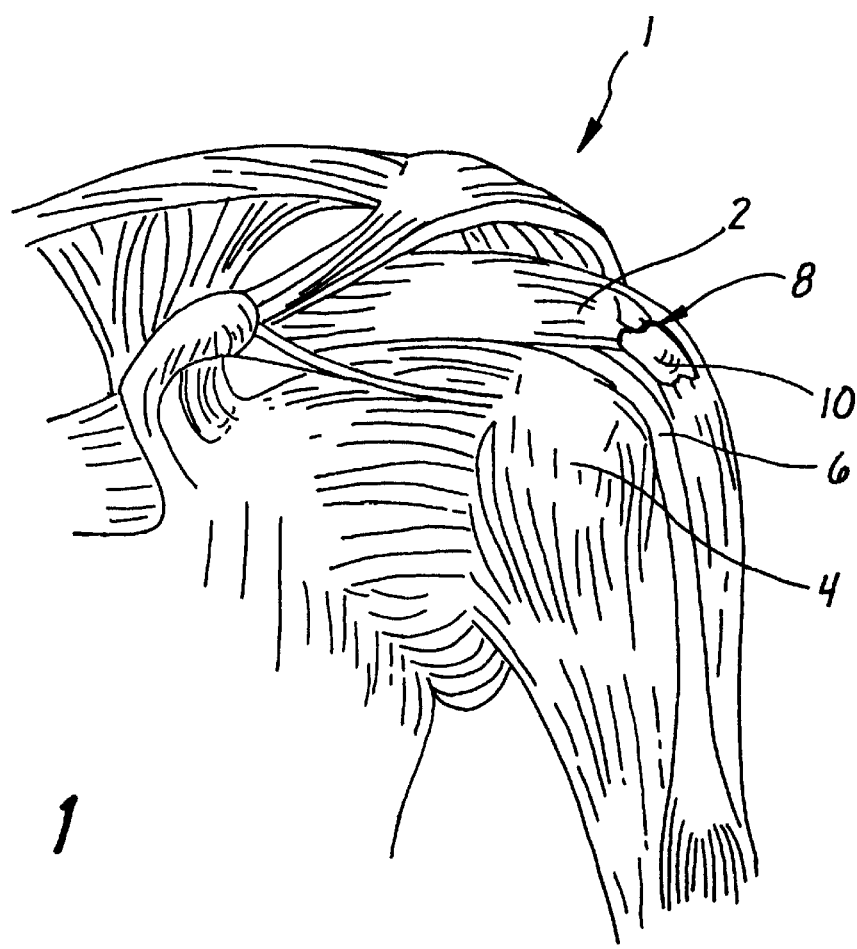
FIG. 1 illustrates a torn rotator cuff.

Referring now to FIG. 1, there is shown representative shoulder musculature 1, including a supraspinatus muscle 2, a deltoid muscle 4, a biceps tendon 6, a torn rotator cuff 8, and a humeral head 10. The humeral head 10 is not normally visible, as it is typically covered by the rotator cuff. However, in the illustration, the torn rotator cuff 8 has pulled away from the head 10 of the humerus, exposing it to view.

Figure 2A:
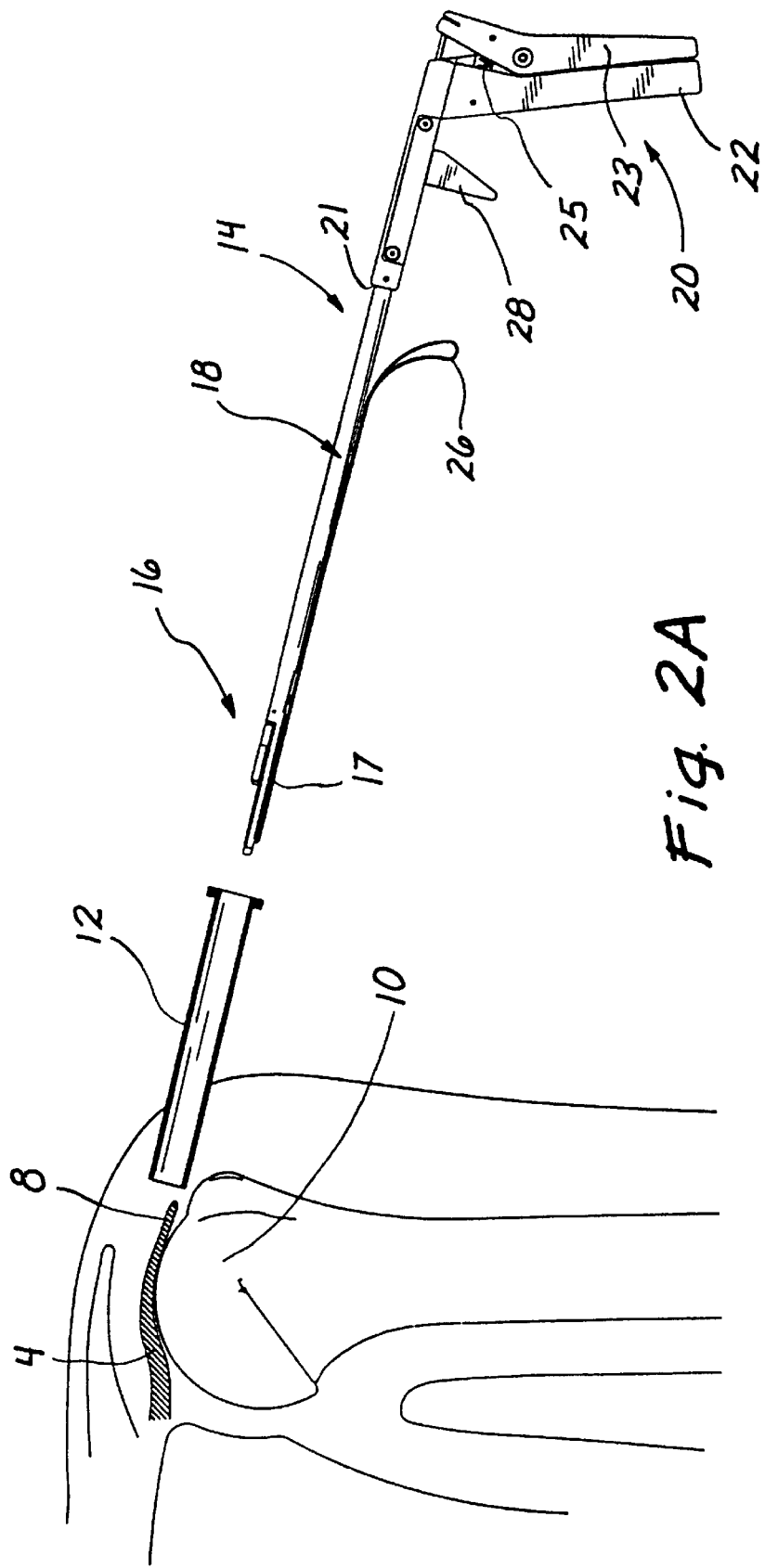
FIGS. 2A through 2E are schematic plan views illustrating one embodiment of the invention, and a method, in sequence, for using same.
Figure 2B:
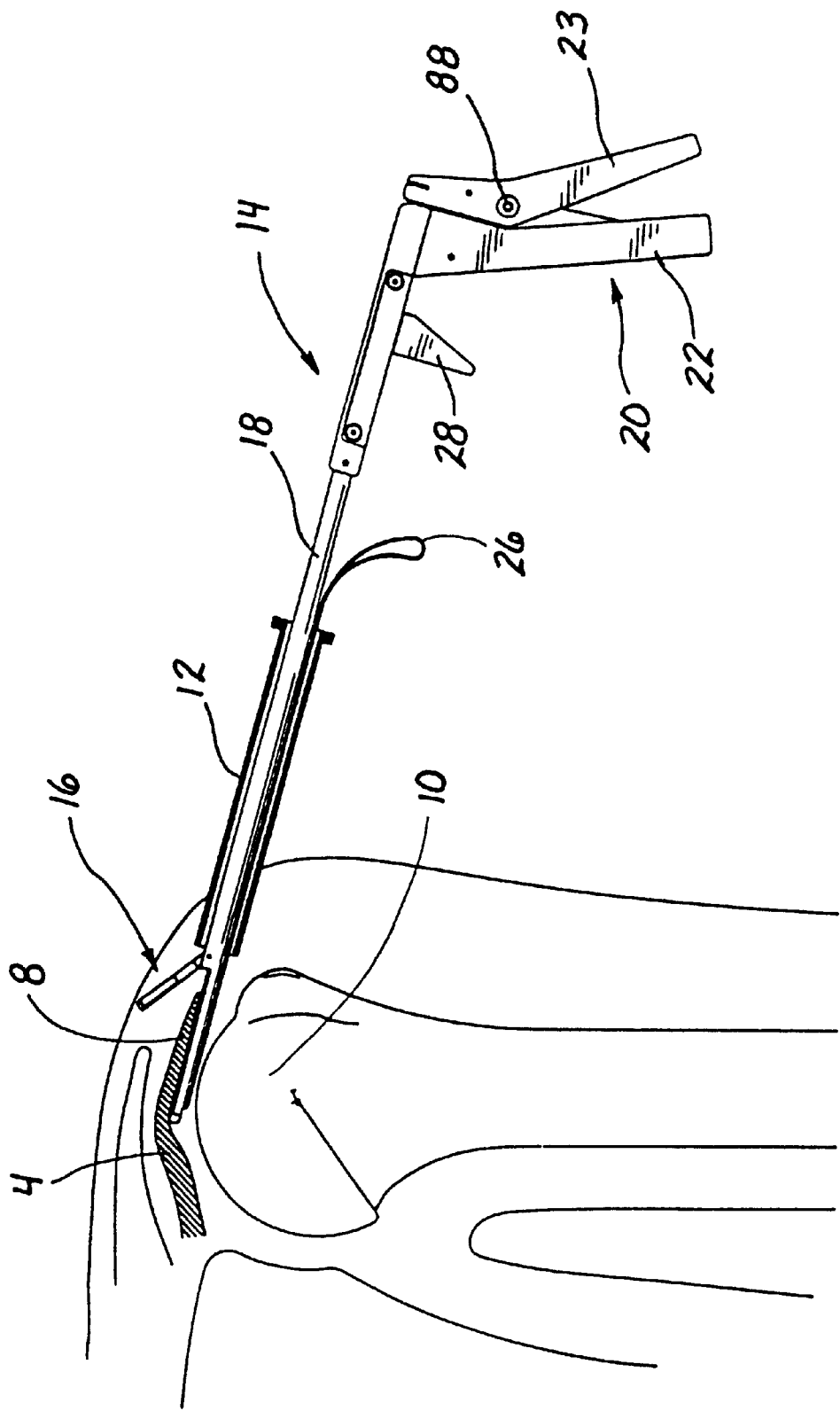

Referring now particularly to FIGS. 2A through 2E, there is illustrated the general structure and function of an embodiment constructed and operated in accordance with the principles of the present invention. A trocar port 12 has been inserted into the shoulder joint, providing a conduit through which a grasper/stitcher 14 may be passed. The grasper/stitcher 14 is provided with pivotable jaws 16 for grasping the torn rotator cuff 8. The jaws 16 are disposed at a distal end 17 of a hollow barrel 18. A handpiece 20 is disposed at a proximal end 21 of the hollow barrel 18, and is adapted to open and close the jaws 16. In the present preferred embodiment, the handpiece 20 comprises a handle grip 22 and a handle lever 23, which pivots about a pivot pin. In a manner to be fully described below, the handle lever 23 is suitably connected to the jaws 16 to actuate the jaws 16 between an open and a closed position, depending upon the position of the handle lever 23. A spring 25 biases the pivotal handle portion to an extended position, as shown in FIG. 2B, wherein the jaws are disposed in an open configuration. Of course, the actuating mechanism which is illustrated for moving the jaws 16 between their open and closed positions, though presently preferred, is only exemplary. Many other types of similar actuating mechanisms are known to those skilled in the art, and any of those would be suitable for the present application.

In FIG. 2A, the grasper/stitcher 14 is shown with the jaws 16 closed, trailing a suture 26, ready to be placed into the shoulder joint through the trocar port 12. To maintain the jaws 16 in their closed position, the operator holds the two handpiece portions 22 and 23 together, against the biasing force of spring 25, using a squeezing action.

FIG. 2B illustrates the grasper/stitcher 14 having been inserted through the trocar port 12 into the shoulder joint, and the jaws 16 having been opened by releasing the handle lever 23 of the handpiece 20, so that the handle lever 23 becomes biased away from the handle grip 22, thereby actuating the jaws 16 to an open position. The jaws 16 are oriented such that the torn rotator cuff 8 is situated between the jaws 16.

Figure 2C:
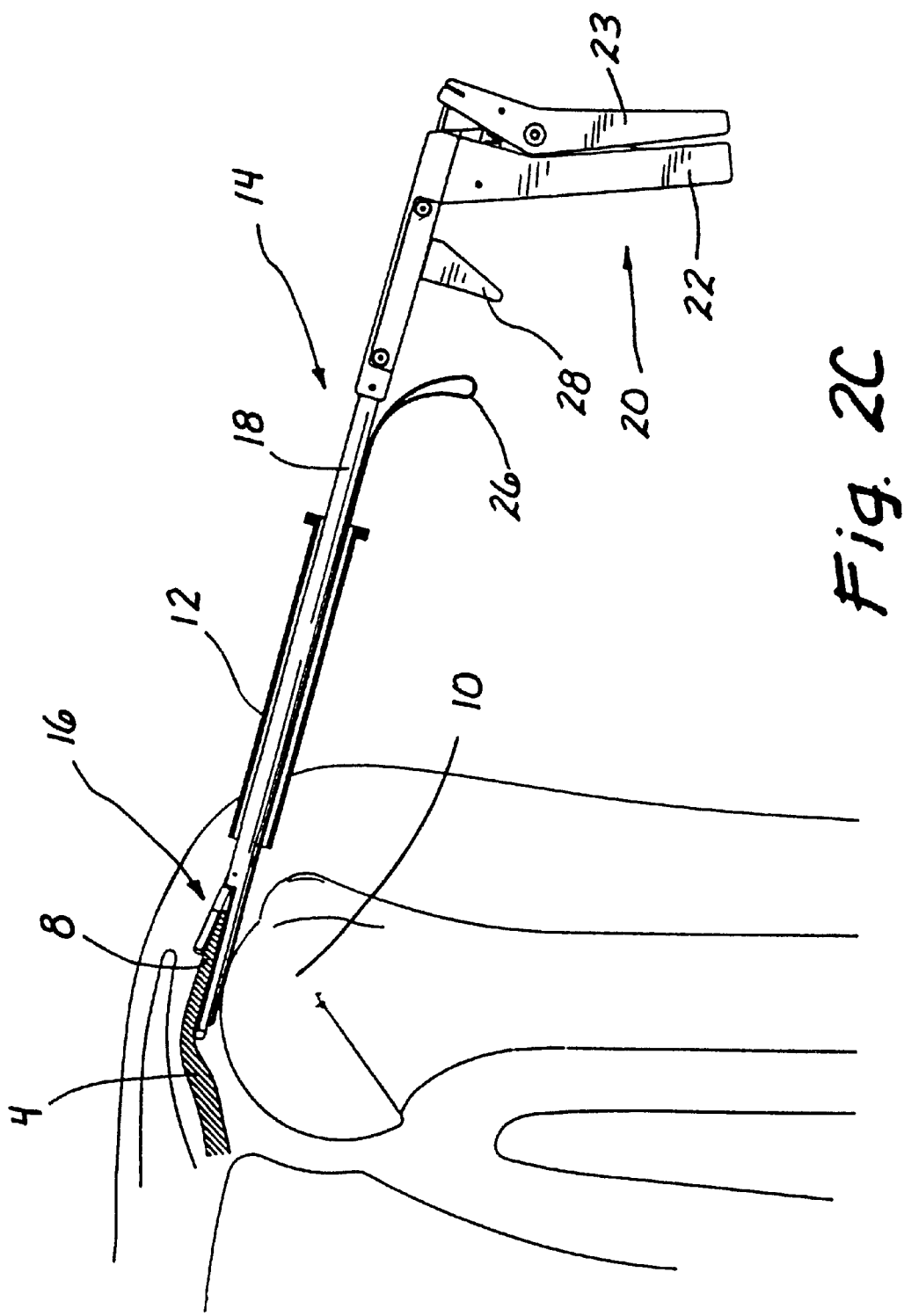
Figure 2D:
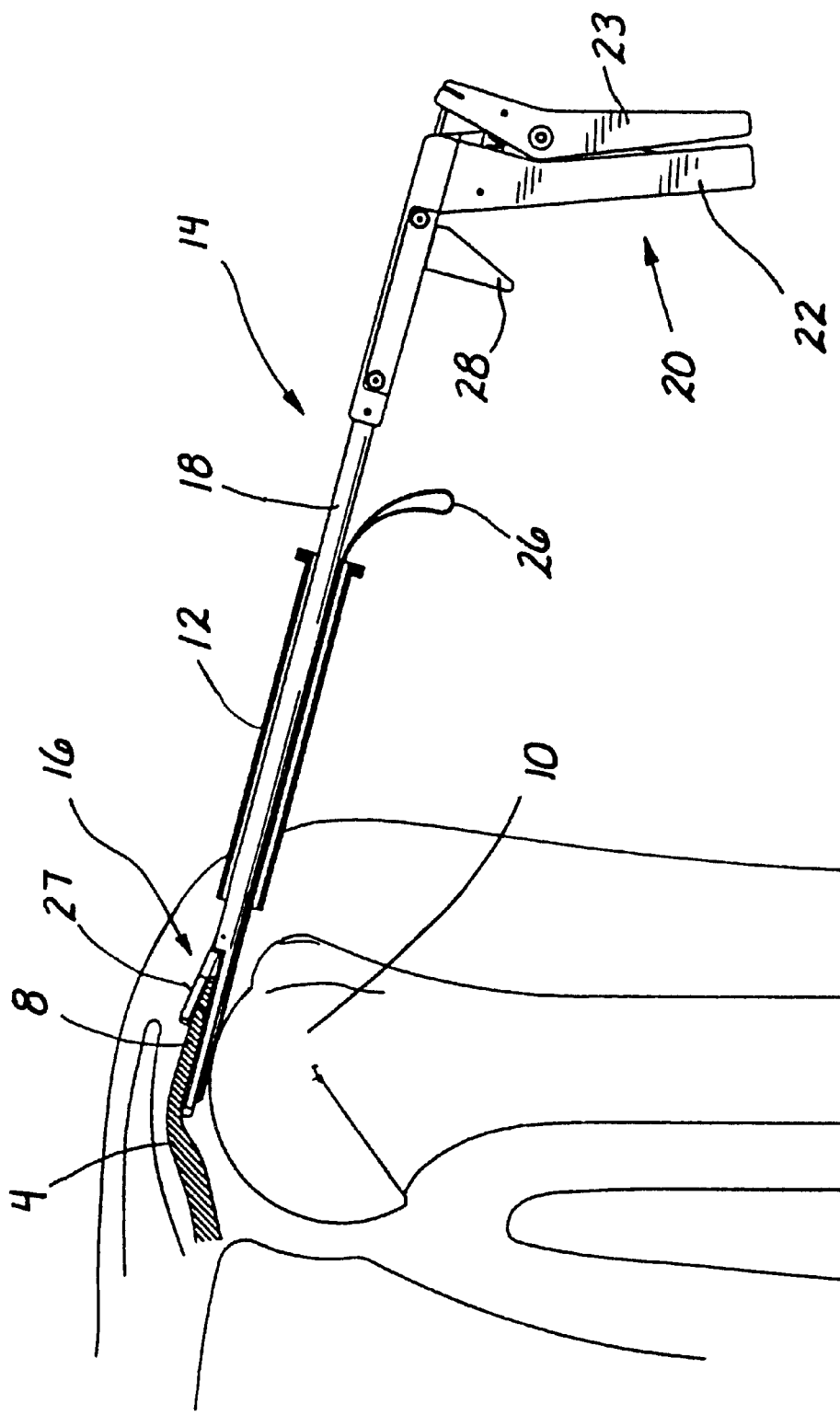
Figure 2E:
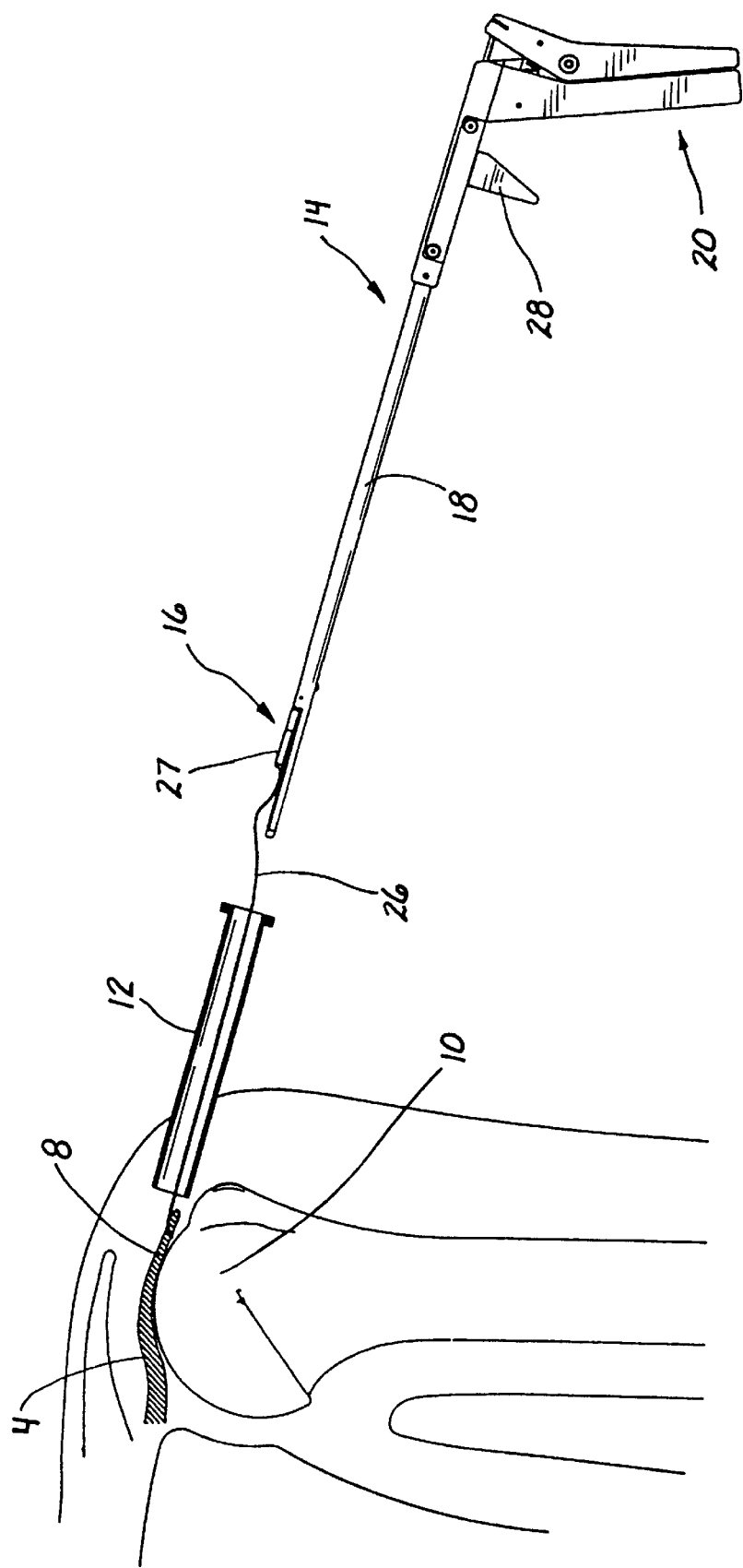

As shown in FIG. 2C, the hand piece 20 is again actuated to pivot and close the jaws 16, to thereby grasp the tissues of the torn rotator cuff 8. Referring now to FIG. 2D, it is seen that needles 27 have been drawn through the tissues of the torn rotator cuff 8 by rearward movement of a trigger 28. The needles 27 are captured by the jaws 16, and, as the grasper/stitcher 14 is withdrawn proximally from the operative site, the suture 26 is drawn along with the grasper/stitcher 14 and through the tissues of the torn rotator cuff 8, forming a mattress stitch in the torn tendon 8 (FIG. 2E).

Figure 4:
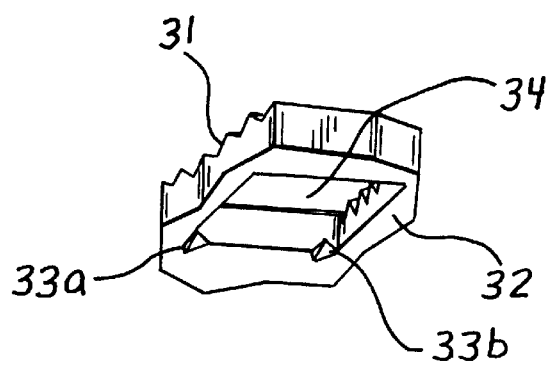
FIG. 4 is a detail perspective view, in isolation, of the underside of the needle guide portion of the present invention.
Figure 3:
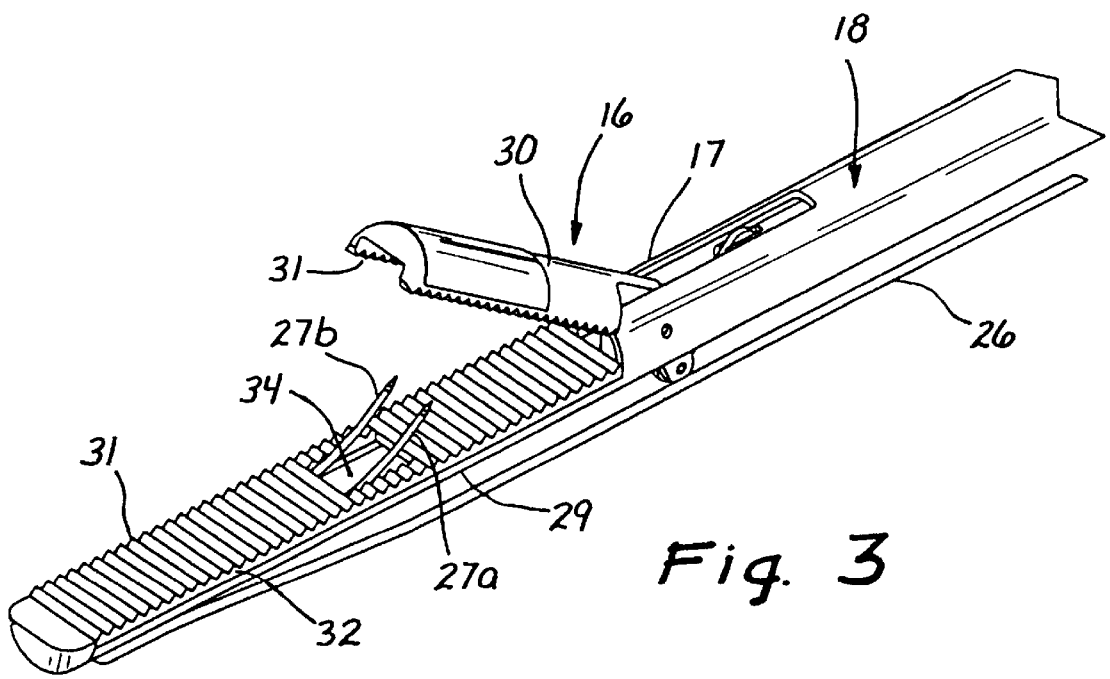
FIG. 3 is a detail perspective view of the jaws of the grasper portion of the present invention.

Referring now to FIG. 3, the construction and operation of the grasper/stitcher 14 will be more particularly discussed. The jaws 16, disposed at the distal end 17 of the hollow barrel 18, include a stationary lower jaw 29 and a moveable upper jaw 30. Both jaws 16 include teeth 31 which are configured to atraumatically grip tissue such as the torn rotator cuff 8 shown in FIGS. 1 and 2A–2E. Referring now to both FIGS. 3 and 4, it may be seen that the stationary lower jaw 29 is comprised of several elements, including a jaw plate 32 which includes the teeth 31 and needle guides or channels 33 a,b which are best seen in FIG. 4. The needle guides 33 a,b are disposed on the bottom edge of an enclosed aperture 34. The enclosed aperture 34 allows passage of suture needles 27 a,b therethrough. The needle guides 33 provide a track for the suture needles 27 to ride in, thereby correctly orienting the needles. The stationary lower jaw 29 also includes a removable end cap 36 which will be discussed in further detail below.

Figure 5:
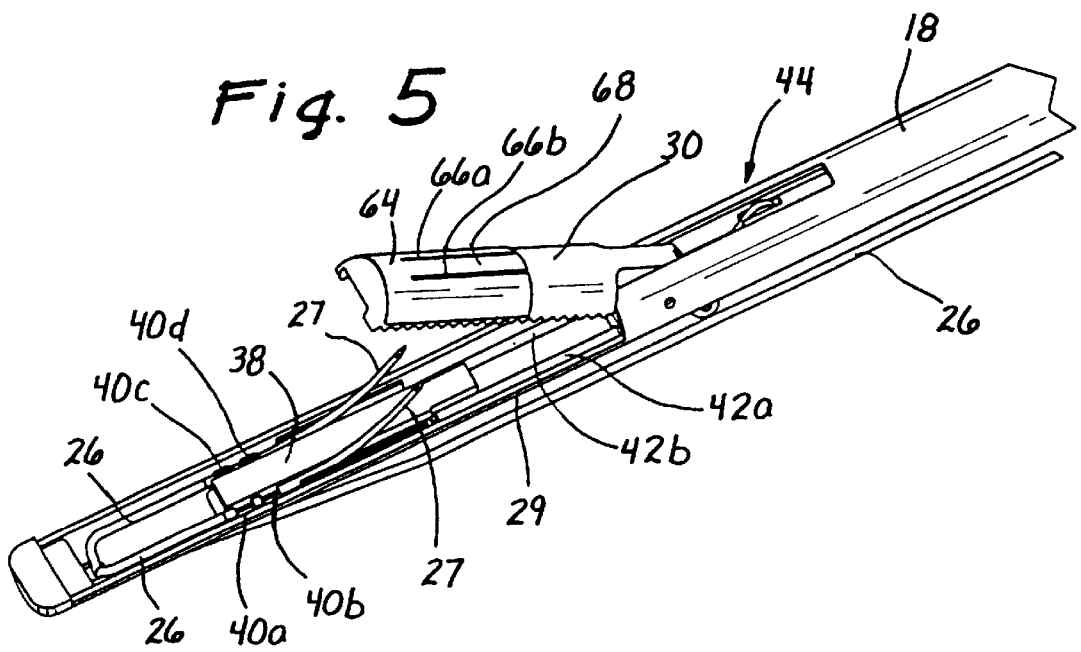
FIG. 5 is a detail perspective view, similar to FIG. 3, of the jaws of the grasper portion of the present invention, with the needle guide removed for clarity.
Figure 6C:
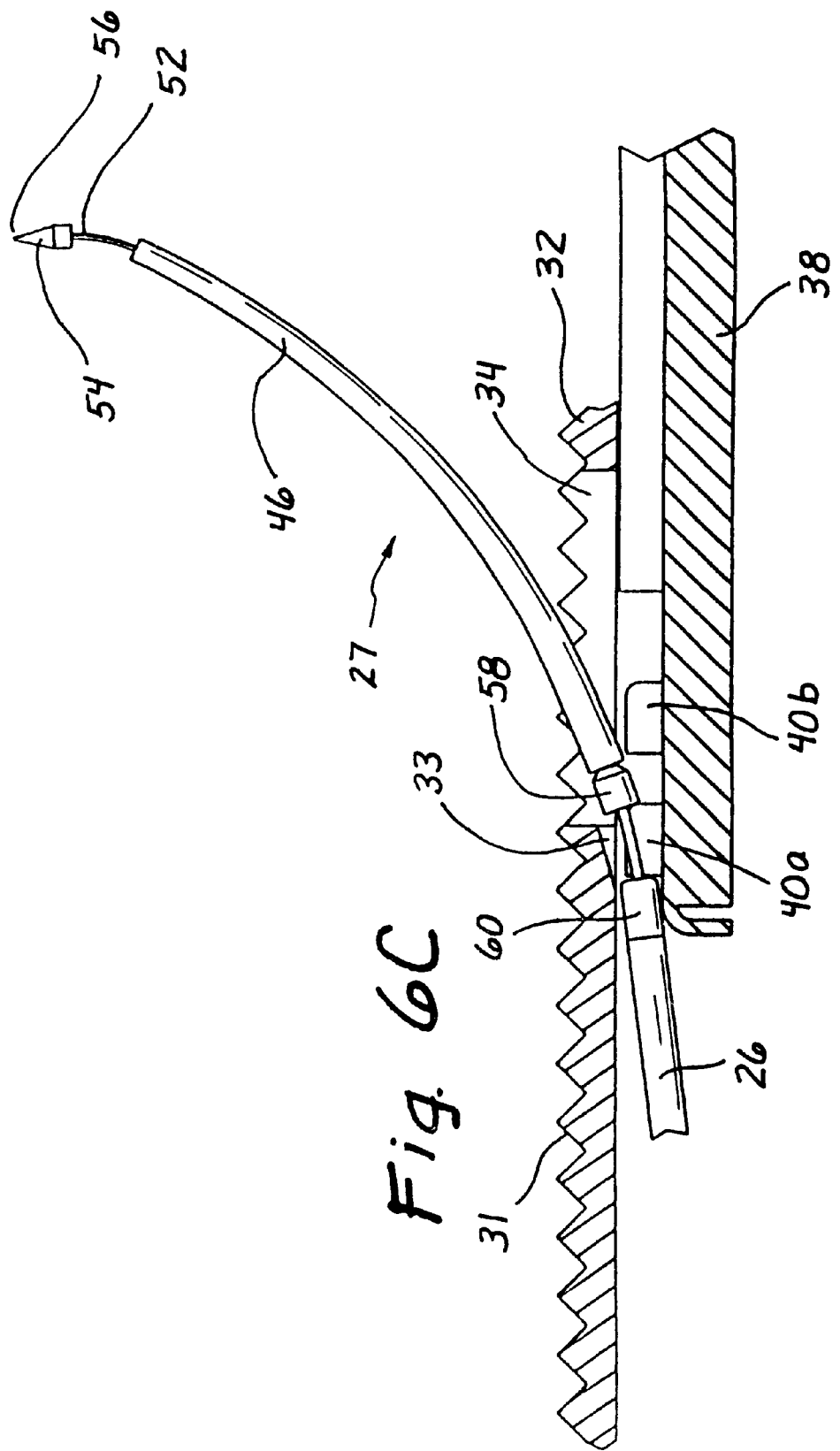

Referring now to FIG. 5, the jaw plate 32 has been removed in order to show a needle carriage 38, which is slidably disposed within the stationary lower jaw 29 formed at the distal end of the hollow tube 18. The needle carriage 38 has capture tabs 40 a,b,c,d located on its distal end. The capture tabs 40 are used to couple the needle carriage 38 with the suture needles 34. The proximal end of the needle carriage 38 is affixed to a slide cable 42 a,b. Slide cable 42 is forked on its distal end to allow it to pass on either side of a linkage 44, which is used to activate the movable upper jaw 30. Referring to FIG. 6A it may be understood that for clarity only one suture needle 27 is shown, but that any description of the single needle is understood to apply to both suture needles 27 a,b. Accordingly, there may be seen a suture needle 27 which includes a curved outer sleeve 46 tapered from a larger diameter at its proximal end to a smaller diameter at its distal end. A ribbon 48 is sidably and coaxially disposed within the curved outer sleeve 46. Referring to FIG. 7, it may be seen that the flexible inner ribbon 48 is circular at its proximal end 50, and transitions into a rectangular shape at its distal end 52. The flattened ribbon shape disposes the flexible inner ribbon 48 to bend in a pre-defined orientation suitable for this application. Referring back now to FIGS. 6A–6D, the distal end 52 of the flexible inner ribbon 48 is permanently attached to a penetrating tip 54. The penetrating tip 54 is tapered to a sharp point 56 at its distal end, to facilitate penetration into tissue. As it may be appreciated by those skilled in the art, there are many different designs and configurations of needles adapted for passing through tissue, including both sharp and blunt tips. It is to be understood that any of these tip designs may be accommodated in the present invention. A needle stop 58 is affixed to the flexible inner ribbon 48 at a predetermined distance from the proximal end of the curved outer sleeve 46. A needle shoulder 60 is affixed to the flexible inner ribbon 48 at a predetermined distance from the proximal end of the needle stop 58. A length of suture 26, which may be constructed from any material known in the art as suture material, for example braided polyester, is permanently attached to the proximal end of the needle shoulder 60.

Now with reference back to FIG. 5, it may be seen that the movable upper jaw 30 includes a needle catch 64 attached to its outer surface. The needle catch 64 further comprises elongated apertures 66 a,b, which are formed by a tab 68. When the jaws 16 are in a position of grasping tissue as shown in FIG. 8, the movable upper jaw 30 and the stationary lower jaw 29 are aligned to allow for the suture needles 34 to pass through the apertures 66 a,b in the needle catch 64. How the needle catch 64 captures the suture needles 27 will be explained in more detail below.

As illustrated in FIG. 8, the linkage 44 includes a pin 70, a link 72, a pin 74, a jaw cable 76, and a second pin 78. The movable upper jaw 30 is rotatably attached to the hollow barrel 18 by means of the pin 70. The proximal end of the movable upper jaw 30 is rotatably attached to the distal end of the link 72 using the pin 74. The proximal end of the link 72 is then rotatably attached to the jaw cable 76 using the pin 78. The movable upper jaw 30 pivots about the pin 70 when activated by the jaw cable 76.

The actuation mechanism that causes the jaw cable 76 to move will now be described in greater detail. As shown particularly in FIG. 9, the jaw cable 76 passes through the proximal end of hollow barrel 18 to the handpiece 20. The proximal end of the jaw cable 76 is attached to the handle lever 23 by means of a pin 82 which is slidably disposed within a slot 84 at the top of the handle lever 23. The handpiece 20 includes the handle lever 23, the handle grip 22 and a pivot pin 88. The handle lever 23 is pivotally attached to the handle grip 22 using the pivot pin 88. The extension spring 25 is attached to the handle lever 23 by way of a pin 92. The other end of the extension spring 25 is attached to the handle grip 22 by way of a pin 94. The handle lever 23 is normally in an open position, due to force pulling on it by way of the extension spring 25. This means that the movable upper jaw 30, located at the distal end of the device, is in a normally open position due to the spring force.

Figure 9:
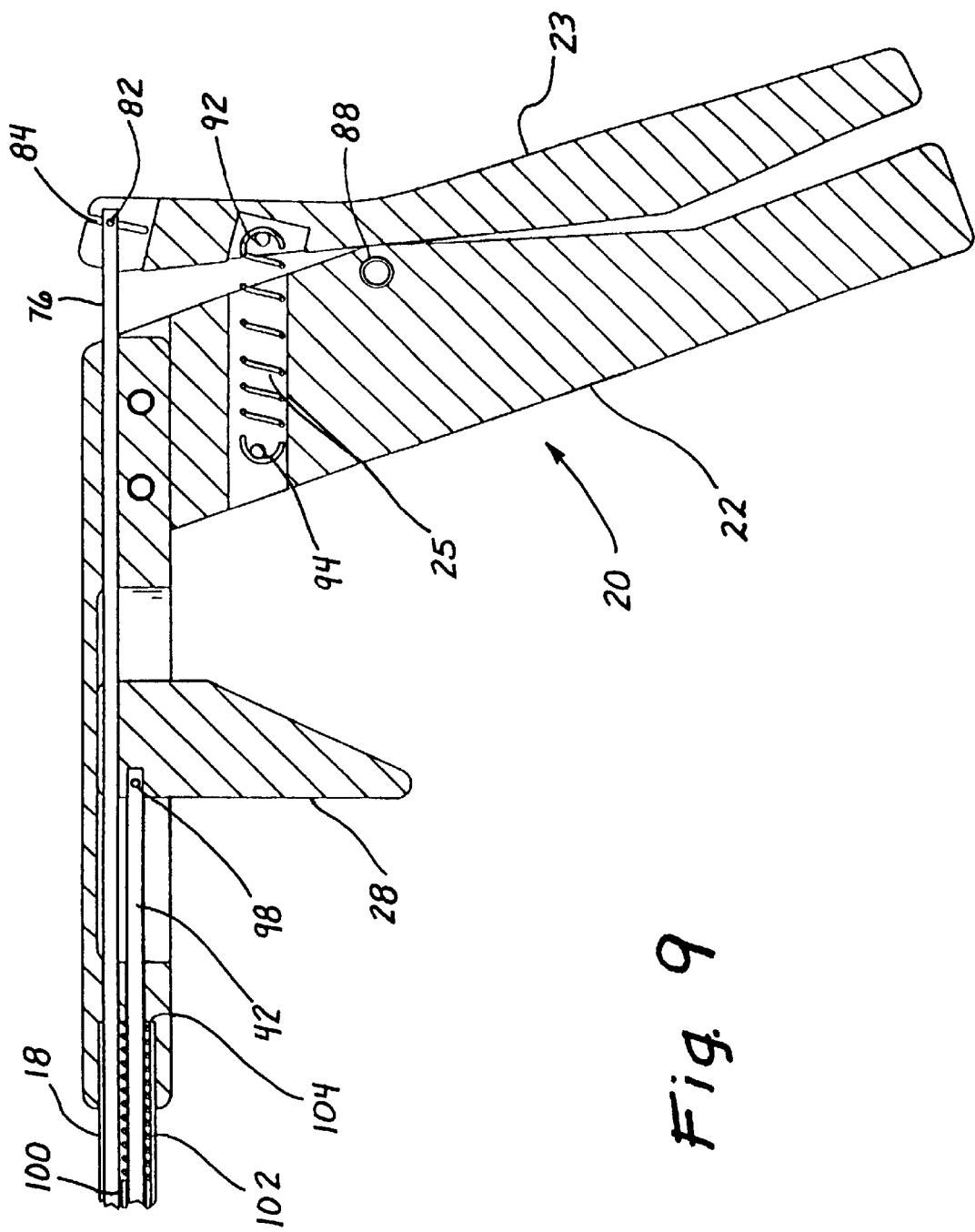
FIG. 9 is a side, partial cross-sectional view of the handle of the present invention.

As shown in FIG. 9, the slide cable 42, previously described in reference to FIG. 5, passes through the proximal end of the hollow barrel 18 to the handle 20. The proximal end of the slide cable 42 is attached to the trigger 28, using a pin 98. An outer sleeve 100 is slidably and co-axially placed over the slide cable 42. A compression spring 102 is slidably and co-axially placed over the slide cable 42 and abuts the outer sleeve 100 on one end, and a spring land 104 on the other end. The compression spring 102 provides a return force to the trigger 28 and consequently to the needle carriage 38 after deployment of suture needles 34.

In a preferred method of the present invention the grasper/stitcher 14 is inserted through a portal in the shoulder, as shown in FIG. 2B. The portal is opened by first making an incision in the skin then inserting the trocar port 12 through the incision to the repair site. The distal end of the hollow barrel 18 is inserted through the cannula until the jaws 16 reach the torn rotator cuff tissue 8. In operation, the distal end of the grasper is positioned at the repair site against the tissue to be grasped. Moveable jaw 30 is advanced toward the stationary jaw 29 by squeezing handle lever 23. As lever 23 moves inwardly by pivoting about pivot pin 88, the jaw cable 76 is drawn rearwardly, proximal of the handpiece 20. When the jaw cable 76 is retracted rearwardly, the movable jaw 30 pivots toward the stationary jaw 29 to close the jaws. Once the appropriate section of tissue is isolated and grasped by jaws 16, the lever 23 may be locked in its closed position, using a latch mechanism (not shown).

Once the surgeon is satisfied with the placement of the grasper 14, the surgeon can then deploy the suture needles to create a mattress stitch in the torn rotator cuff 8. In operation, the suture needles 27 are advanced through the rotator cuff by pulling on the trigger 28. This action draws the slide cable 42 rearwardly towards the proximal end of the grasper. As the slide cable 42 is pulled rearwardly, it is pulled against the force of return spring 102. As the slide cable 42 moves rearwardly, it pulls the needle carriage 38 and suture needles 27 proximal to the needle guide aperture 33 (FIG. 6A). The suture needles 27, as they clear the distal edge of the aperture 34, begin to penetrate through the underside of the rotator cuff 8 and advance upwardly towards the movable jaw 30.

Referring now again to FIGS. 6A–6D, the needles are illustrated at various stages of advancement through the rotator cuff In FIG. 6A, the proximal end of the suture needles 27 are fully engaged in the locking tabs of the needle carriage 38. As the suture needles 27 near the end of the ejection stroke, the distal end of the needles 27 pass through the upper movable jaw 30 and the needle catch 64. As the needles pass through the upper jaw 30, they begin to separate from the needle carriage 38 (FIG. 6B).

Figure 6D:
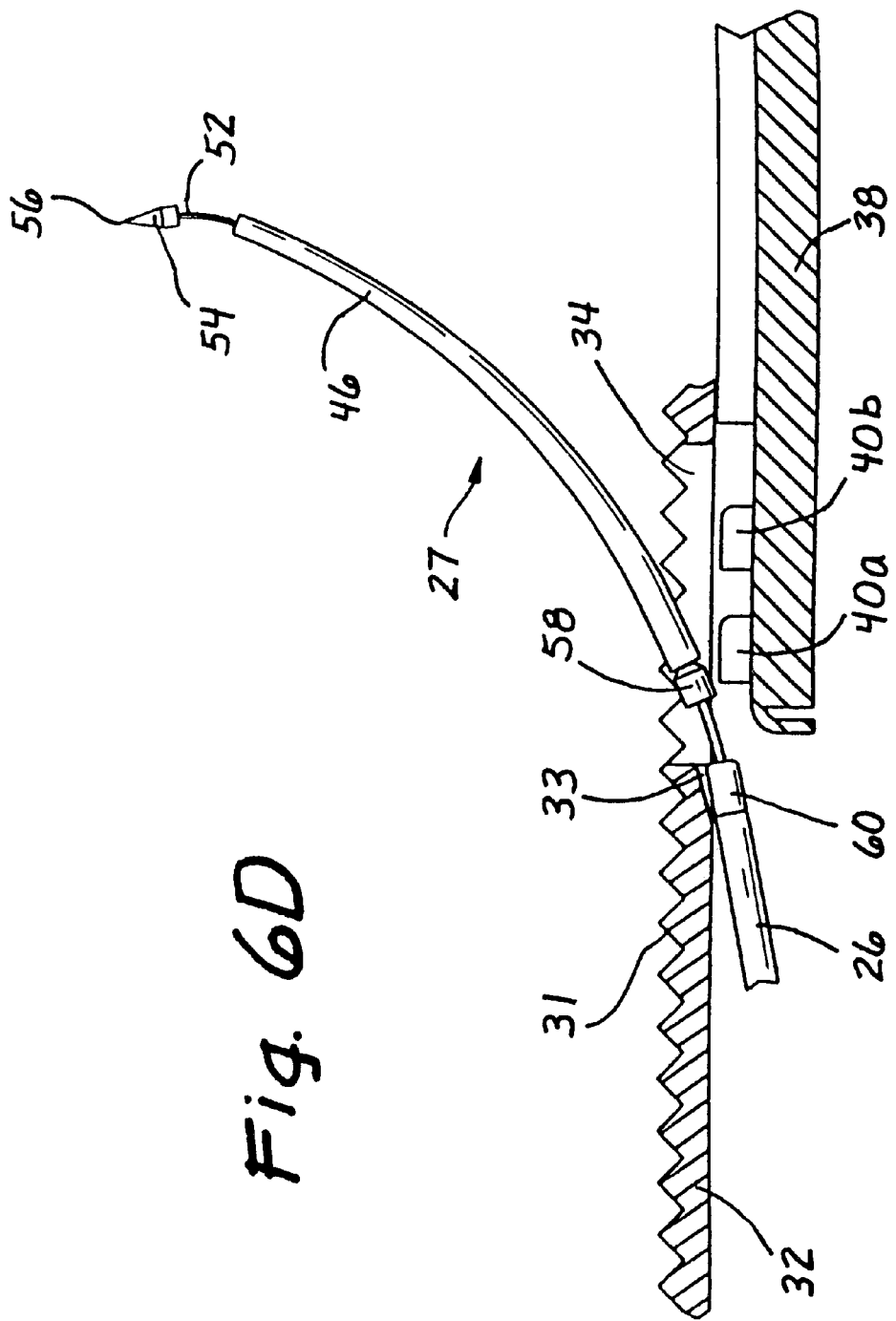

As the proximal end of the needle's curved outer sleeve 46 separates from the first tab on the needle carriage 38, there is no further force pushing on it to force it through the rotator cuff 8. The force now pushing on the suture needle 27 is concentrated on the needle stop 58. As the carriage 38 is advanced further, the needle's curved outer sleeve 46 remains stationary due to the resistance caused by contact with the tissue of the rotator cuff 8. However, the needle ribbon 48 is free to advance further. As shown in FIG. 6C, the gap between the needle's curved outer sleeve 46 and the needle stop 58 begins to close until there is no gap at all. At this point the penetrating tip 54 has extended beyond the distal end of the needle's curved outer sleeve 46. Once the gap is closed between the needle stop 58 and the outer sleeve 46, the needle will again continue to advance as one unit through the rotator cuff 8. As the needle carriage 38 advances further, it pushes on the suture needle 27 until the needle has been pushed beyond the point of contact with the needle carriage 38 (FIG. 6D). At this point the suture needles 27 extend through the torn rotator cuff 8 and protruding through the upper movable jaw 30 and needle catch 64. Due to a pre-defined curve in the needle's ribbon 48, the penetrating tip 54 remains extended from the distal end of the needle's curved outer sleeve 46.

At this point, any pull force being applied by the grasper 14 on the rotator cuff 8 is relaxed. Once the rotator cuff is in a relaxed state, the jaws of the grasper 14 are then opened. The handle lever 23 is unlocked from the locking mechanism (not shown) and returns to an open position due to the pull force exerted on it by means of the return spring 25. As the return spring 25 pulls on the lever 23, the handle lever 23 pivots about the pin 88. As the handle lever 23 opens, it pulls on the jaw cable 76 by means of the pin. This advances the jaw cable 76 towards the distal end of the barrel 18. As the jaw cable 76 advances, it pushes on the linkage segment 44, which then pushes on the movable upper jaw 30, causing the upper jaw 30 to pivot about the pin 70 to open and separate away from the stationary jaw 29 (FIG. 8).

Figure 10A:
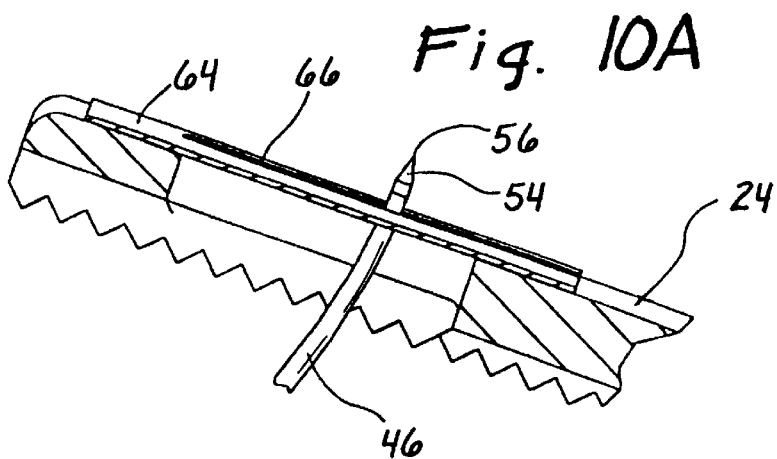
FIGS. 10A through 10C are sequential diagrammatic views, in cross-section, illustrating certain steps of an inventive method for capturing suture needles in the movable upper jaw of the inventive apparatus.

As shown in FIG. 10a, as the movable upper jaw 30 begins to open, the suture needles 27 for the most part remain stationary due to resistance caused by their contact with the tissue of the rotator cuff 8. As the upper jaw 30 is opened, it slips pass the suture needles 27. At a point just beyond the distal end of the suture needle's curved outer sleeve 46, the needle catch 64 on the upper jaw 30 trap the suture needles 27 at a point between the curved outer sleeve 46 and the penetrating tip 54.

Figure 10B:
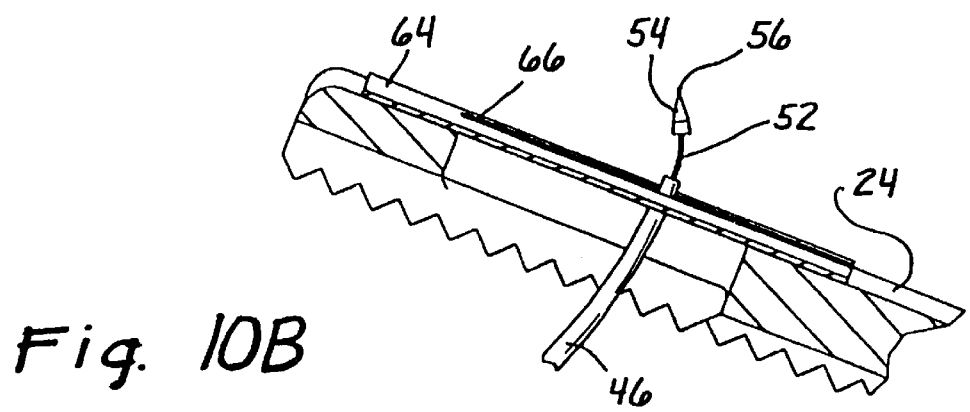

Now, with reference to FIG. 10b, it is seen that the upper jaw 30 slips pass the needle's outer sleeve 46. The aperture or slit 66 in the needle catch 64 is allowed to close down around the needle's ribbon 48. The slit 66 is large enough that it does not restrict the movement of ribbon 48, but is sufficiently small so that it does not allow the penetrating tip 54 to pass back through. This is because the needle catch 64 on the upper jaw 30 can only be deflected in an outward direction, away from the outer surface of the upper jaw 30. Thus, now that the distal end of the suture needles 27 are trapped in the needle catch 64 on the upper jaw 30, they are pulled through the rotator cuff as the upper jaw 30 is opened further.

Figure 10C:
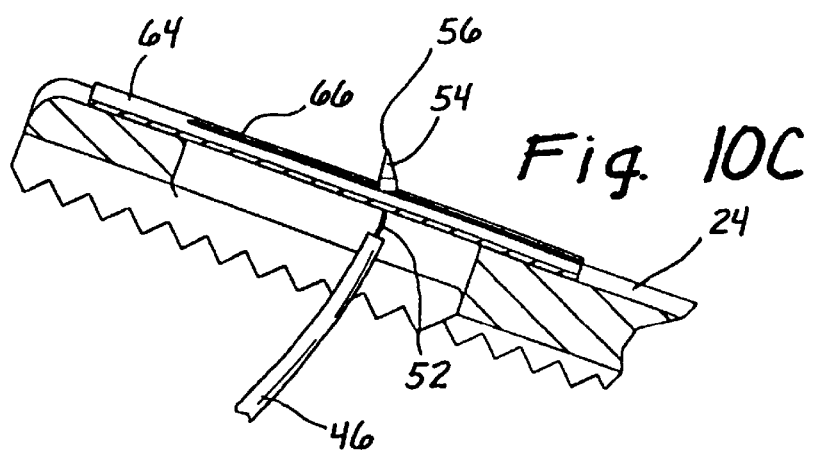
Figure 14:
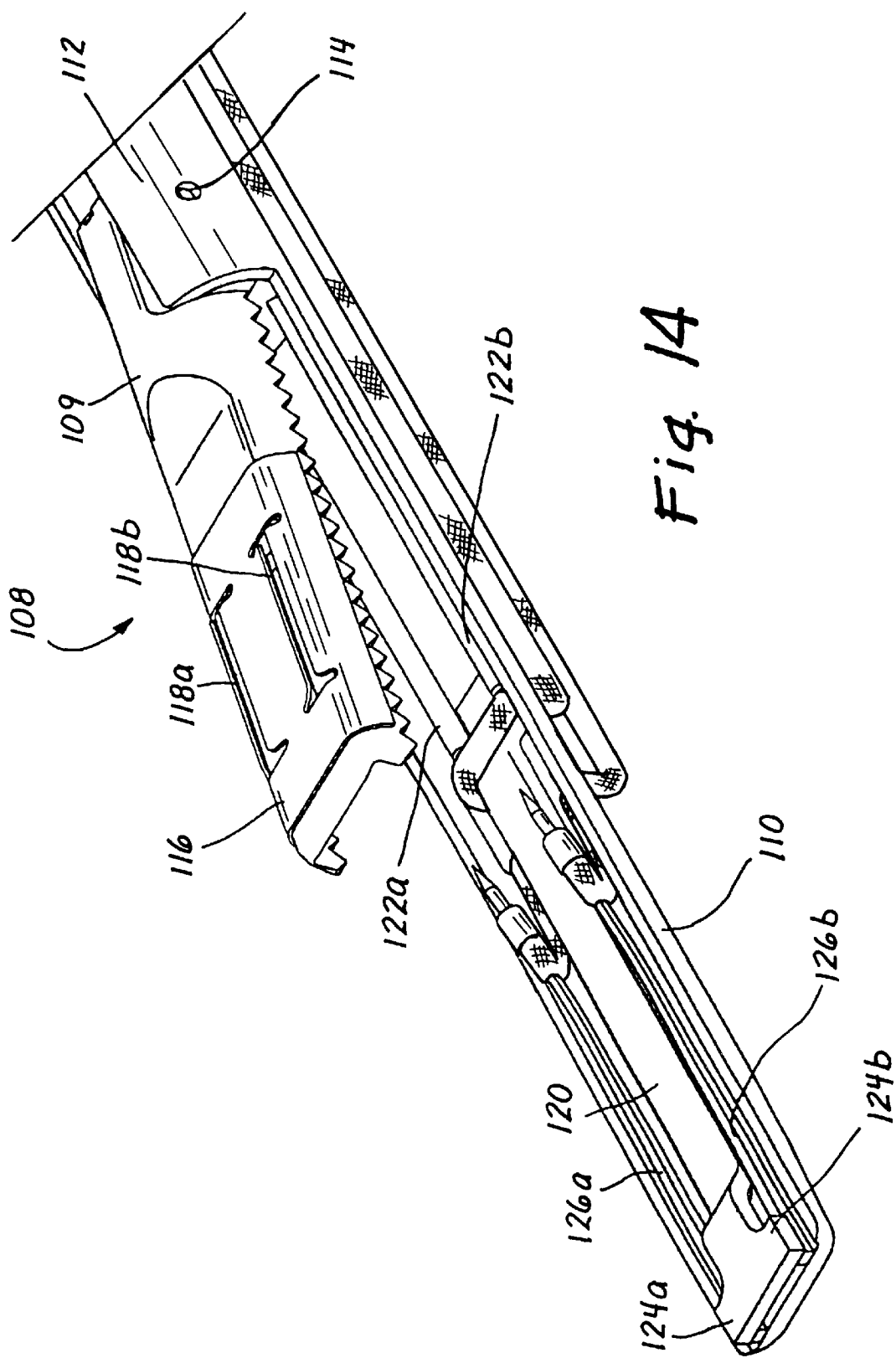
FIG. 14 is a detail perspective view of the interior of the distal end of an alternate embodiment of the suturing device of the invention.

As shown in FIG. 10c, when the jaws 16 of the grasper 14 are fully extended, the suture needles 27 are nearly pulled through the rotator cuff 8. To complete the pull out of the suture needles 27, it is necessary to pull on the grasper 14, and to begin to remove it from the repair site.

Now with reference particularly to FIG. 11, once the suture needles 27 are extended through the rotator cuff 8, they can be secured by closing down the jaws 16 of the grasper 14. Then, the graspers can be retracted back through the portal via the trocar cannula 12 (FIGS. 2D and 2E).

As shown in FIG. 12, the next step in the preferred method is to pull on the free ends 105 of the suture 26. This causes the suture to pass through the rotator cuff 8 at puncture sites 106a and 106b. As the suture is pulled through, the loop end 107 of the suture is pulled snug against the underside of the rotator cuff 8 to form what is referred to as a mattress stitch. This process is repeated as necessary, depending on the number of bone anchors required to repair the rotator cuff for a given surgical procedure.

To reload the inventive instrument with new suture needles 27, the end cap 36 is pulled off to provide necessary access, as shown in FIG. 13. After the end cap 36 is removed, the needle carriage 38 can be advanced beyond the distal end of the barrel 18 to be reloaded. To advance the needle carriage 38 in this manner simply requires advancing the handle trigger 28 towards the distal end of the grasper 14. Once new suture needles are reloaded, the end cap 36 can be replaced. The remaining suture to form the next stitch passes through the lower stationary jaw 29 through a small notch abutting the end cap (not shown). This extra length of suture may be left outside the body as the grasper 14 is inserted back through the portal 12 to the operative site.

A second, modified embodiment of a suturing instrument constructed in accordance with the principles of the present invention is illustrated in FIGS. 14–17. With respect to this embodiment, it is to be understood that the proximal portion of the device is substantially the same as that illustrated with respect to the earlier embodiment, and is therefore not shown. Thus, in FIG. 14, there is seen a distal end 108 of the inventive suturing device, which includes a moveable upper jaw 109, a stationary lower jaw 110, and a body 112. The moveable upper jaw 108 is pivotally attached to the body 112 via a pin 114, and includes a ferrule catch 116 which further includes slits 118 a,b. The ferrule catch 116 is preferably constructed of a high temper spring steel suited for tissue contact. By way of example only, ANSI 301 spring temper steel is suitable for this application. A needle carriage 120 is slidably disposed on the lower stationary jaw 110. The needle carriage 120 is permanently affixed to slide cables 122 a,b, and moves proximally from a distal position to a proximal position within the lower stationary jaw 110 when urged by the slide cables 122. The needle carriage 120 includes tabs 124 a,b to which are coupled needles 126 a,b.

Figure 17:
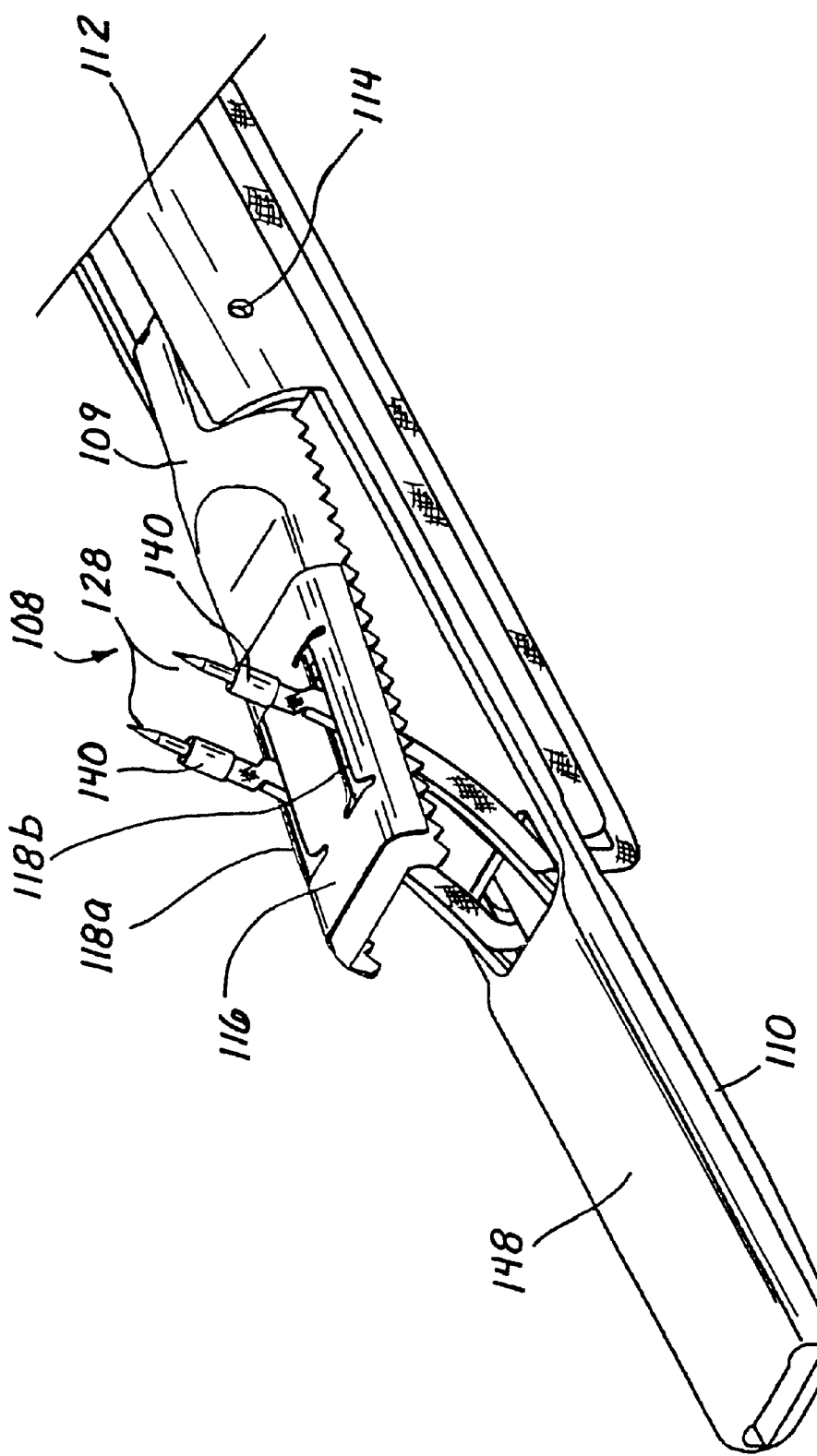
FIG. 17 is a detail perspective view of the inventive embodiment shown in FIGS. 14–16.

The needles 126 may be constructed, as is well known in the art, of 300 or 400 series stainless steel. As shown in FIGS. 15–17, each needle 126 includes a sharpened tip 128, a bulge 130, and a body 132. The bulge 130 may be best seen by referring to FIG. 16, where a suture 134 comprising a hollow inner lumen 136 and a distal end 138 may also be seen. The distal end 138 is encapsulated by a ferrule 140. The ferrule 140 is further comprised of an outside diameter 142, an inside diameter 144, and a shoulder 146. The distal end 138 of the suture 134 is passed into the ferrule 140 and crimped or otherwise mechanically or adhesively attached to the ferrule 140.

In operation, the body 132 of the needle 126 is threaded into the hollow inner lumen 136 of the suture 134 and through the inside diameter 144 of the ferrule 140. The bulge 130 interferes with the shoulder 146 of the ferrule, thereby preventing the ferrule 140, and concomitantly the suture 134, from sliding further along the body 132. Referring now to FIGS. 15A–15C, in particular, the function of the combination of the needles 126 and the suture 134 is illustrated. In FIG. 15A, the needles 126 and the ferrule 140 are enclosed by a housing cap 148. It is to be understood that, for clarity, he tissue that would normally be grasped between the moveable upper jaw 109 and the stationary lower jaw 110 is not shown. It is also to be understood that FIGS. 15A–15C depict a cross-sectional view showing only one of the two needles 126. Accordingly, and with reference now to FIG. 15B, it may be seen that, as the slide cables 122 are withdrawn as previously described in connection with the prior embodiment, the needle carriage 120 is drawn along a path from the distal to the proximal end of the stationary lower jaw 110. The needles 126, being fixedly attached to the needle carriage 120, are urged to exit the stationary lower jaw 110 and to transit along a curved path described by the pre-configured ben in the needles 126 until penetrating the catch 116 at the slits 118. The ferrule 140 is forced to traverse the slits 118 by the urging of the bulge 130 on the shoulder 146. As the tension on the slide cables 122 is released, the needle carriage 120 is permitted to return to its original position by reversing its motion so that it travels distally. As shown in FIG. 15C, the transition of the needle carriage 120 back to its original position functions to cause the needles 126 from the hollow inner lumen 136 of the suture 134 and from the inside diameter 144 of the ferrule 140, leaving the ferrule 140 trailing the suture 134 to be captured by the ferrule catch 116. This may be seen most advantageously by reference to FIG. 17.

At this point, with the suture 134 and the ferrules 140 captured, the tissue grasped by the moveable upper jaw 109 may be released, and the instrument withdrawn from the operative site, trailing the suture loop stored within its bounds. The result of the execution of these method steps is the creation of a mattress stitch in the grasped tissues in a manner similar to that described with respect to the embodiment illustrated in FIGS. 2–13.

The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suturing device for use endoscopically, comprising:
   a first jaw member,
   a second jaw member, said first and second jaw members being disposed at a distal end of said suturing device;
   an actuator disposed at a proximal end of the suturing device, for actuating the first and second jaw members between a closed orientation, wherein distal ends of the jaw members are disposed in close proximity to one another, and an open orientation, wherein said distal jaw member ends are substantially spaced from one another;
   a hollow barrel disposed between said actuator and said first and second jaw members;
   a linking member disposed within said hollow barrel, connecting said actuator with one of said first and second jaw members;
   a needle carriage which is axially movable between distal and proximal positions at said distal end of said suturing device; and
   at least one needle disposed at the distal end of said suturing device, on said needle carriage, said at least one needle being movable between a retracted position and an extended position for passage through tissue grasped between said first and second jaw members.

2. The suturing device as recited in claim 1, wherein said linking member comprises a cable.

3. The suturing device as recited in claim 1, wherein said first and second jaw members are pivotally connected to one another.

4. The suturing device as recited in claim 1, wherein only one of said first and second jaw members moves when said actuator actuates the jaw members between said closed and said open orientations.

5. The suturing device as recited in claim 1, wherein said actuator comprises a handpiece.

6. The suturing device as recited in claim 5, wherein said handpiece comprises a handle grip and a handle lever, said handle lever being movable relative to said handle grip.

7. The suturing device as recited in claim 6, wherein said handle lever is pivotally connected to said handle grip, and is pivotable between a first position corresponding to said closed orientation of said first and second jaw members and a second position corresponding to said open orientation of said first and second jaw members.

8. The suturing device as recited in claim 7, and further comprising a spring for biasing the handle lever in one of said first and second positions.

9. The suturing device as recited in claim 8, wherein said spring biases said handle lever in said second position.

10. The suturing device as recited in claim 1, wherein said needle carriage is permanently secured to said distal end of said suturing device.

11. The suturing device as recited in claim 1, wherein said needle carriage is removably secured to said distal end of said suturing device.

12. The suturing device as recited in claim 11, wherein capture tabs removably secure said needle carriage to said distal end of said suturing device.

13. The suturing device as recited in claim 1, and further comprising a second actuator disposed at the proximal end of said suturing device, for actuating said needle carriage to move axially between said distal and proximal positions.

14. The suturing device as recited in claim 13, wherein said second actuator comprises a trigger.

15. The suturing device as recited in claim 14, and further comprising a slide cable, which links said trigger to said needle carriage.

16. The suturing device as recited in claim 15, wherein said slide cable is biased to return said needle carriage to its distal position.

17. The suturing device as recited in claim 16, and further comprising a spring for biasing said slide cable.

18. The suturing device as recited in claim 1, wherein said needle carriage is disposed on one of said first and second jaw members.

19. The suturing device as recited in claim 18, wherein said one of said first and second jaw members comprises a lower jaw member which is stationary relative to the other of said first and second jaw members.

20. The suturing device as recited in claim 19, wherein said one of said first and second jaw members further comprises a jaw plate, said jaw plate including at least one needle guide for providing a track for said at least one needle to ride in, when said at least one needle travels between said distal and proximal positions.

21. The suturing device as recited in claim 20, wherein said one of said first and second jaw members comprises a removable end cap, for permitting installation of a new needle carriage.

22. The suturing device as recited in claim 19, wherein the other of said first and second jaw members comprises an upper jaw member which is movable relative to the lower jaw member, said upper jaw member including a needle catch having at least one slot thereon for capturing the distal end of the at least one needle when it has been actuated from said distal position to said proximal position.

23. The suturing device as recited in claim 19, wherein suture attached to said at least one needle is enclosed by a ferrule, and the other of said first and second jaw members comprises an upper jaw member which is movable relative to the lower jaw member, said upper jaw member including a ferrule catch having at least one slot thereon for capturing the ferrule enclosing the suture connected to the at least one needle.

24. The suturing device as recited in claim 1, wherein said at least one needle comprises two spaced needles.

25. A suturing device for use endoscopically, comprising:
a first jaw member;
a second jaw member, said first and second jaw members being disposed at a distal end of said suturing device;
an actuator disposed at a proximal end of the suturing device, for actuating the first and second jaw members between a closed orientation, wherein distal ends of the jaw members are disposed in close proximity to one another, and an open orientation, wherein said distal jaw member ends are substantially spaced from one another;
a hollow barrel disposed between said actuator and said first and second jaw members;
a linking member disposed within said hollow barrel, connecting said actuator with one of said first and second jaw members; and
at least one needle disposed at the distal end of said suturing device, said at least one needle being movable between a retracted position and an extended position for passage through tissue grasped between said first and second jaw members, wherein said at least one needle comprises a flexible inner ribbon disposed within a curved outer sleeve.

26. The suturing device as recited in claim 25, wherein a penetrating tip is attached to said flexible inner ribbon.

27. The suturing device as recited in claim 25, wherein said flexible inner ribbon comprises a distal end and a proximal end, said ribbon having a generally circular configuration at its proximal end, transitioning to a generally rectangular configuration at its distal end.

28. The suturing device as recited in claim 25, wherein said curved outer sleeve comprises a distal end and a proximal end, said sleeve having a relatively large diameter at said proximal end, transitioning to a relatively small diameter at said distal end.

29. A suturing device for use endoscopically, comprising;
a first jaw member;
a second jaw member, said first and second jaw members being disposed at a distal end of said suturing device;
an actuator disposed at a proximal end of the suturing device, for actuating the first and second jaw members between a closed orientation, wherein distal ends of the jaw members are disposed in close proximity to one another, and an open orientation, wherein said distal jaw member ends are substantially spaced from one another;
a hollow barrel disposed between said actuator and said first and second jaw members;
a linking member disposed within said hollow barrel, connecting said actuator with one of said first and second jaw members; and
at least one needle disposed at the distal end of said suturing device, said at least one needle being movable between a retracted position and an extended position for passage through tissue grasped between said first and second jaw members, said needle having a distal end and a proximal end, said distal end of said needle being proximal to said proximal end of said needle on said suturing device.

30. A suturing device for use endoscopically, comprising:
a first jaw member;
a second jaw member, said first and second jaw members being disposed at a distal end of said suturing device;
an actuator disposed at a proximal end of the suturing device, for actuating the first and second jaw members between a closed orientation, wherein distal ends of the jaw members are disposed in close proximity to one another, and an open orientation, wherein said distal jaw member ends are substantially spaced from one another;
a needle carriage which is axially movable between distal and proximal positions at said distal end of said suturing device; and
at least one needle disposed on said needle carriage, the axial movement of said needle carriage functioning to move said at least one needle between a retracted position and an extended position for passage through tissue grasped between said first and second jaw members.

31. The suturing device as recited in claim 30, wherein said first and second jaw members are pivotally connected to one another.

32. The suturing device as recited in claim 30, wherein only one of said first and second jaw members moves when said actuator actuates the jaw members between said closed and said open orientations.

33. The suturing device as recited in claim 30, wherein said actuator comprises a handpiece.

34. The suturing device as recited in claim 33, wherein said handpiece comprises a handle grip and a handle lever, said handle lever being movable relative to said handle grip.

35. The suturing device as recited in claim 34, wherein said handle lever is pivotally connected to said handle grip, and is pivotable between a first position corresponding to said closed orientation of said first and second jaw members and a second position corresponding to said open orientation of said first and second jaw members.

36. The suturing device as recited in claim 35, and further comprising a spring for biasing the handle lever in one of said first and second positions.

37. The suturing device as recited in claim 36, wherein said spring biases said handle lever in said second position.

38. The suturing device as recited in claim 30, wherein said needle carriage is permanently secured to said distal end of said suturing device.

39. The suturing device as recited in claim 30, wherein said needle carriage is removably secured to said distal end of said suturing device.

40. The suturing device as recited in claim 39, wherein capture tabs removably secure said needle carriage to said distal end of said suturing device.

41. The suturing device as recited in claim 30, and further comprising a second actuator disposed at the proximal end of said suturing device, for actuating said needle carriage to move axially between said distal and proximal positions.

42. The suturing device as recited in claim 41, wherein said second actuator comprises a trigger.

43. The suturing device as recited in claim 42, and further comprising a slide cable, which links said trigger to said needle carriage.

44. The suturing device as recited in claim 30, wherein said at least one needle comprises a flexible inner ribbon disposed within a curved outer sleeve.

45. The suturing device as recited in claim 44, wherein a penetrating tip is attached to said flexible inner ribbon.

46. The suturing device as recited in claim 44, wherein said flexible inner ribbon comprises a distal end and a proximal end, said ribbon having a generally circular configuration at its proximal end, transitioning to a generally rectangular configuration at its distal end.

47. The suturing device as recited in claim 44, wherein said curved outer sleeve comprises a distal end and a proximal end, said sleeve having a relatively large diameter at said proximal end, transitioning to a relatively small diameter at said distal end.

48. The suturing device as recited in claim 30, said needle having a distal end and a proximal end, said distal end of said needle being proximal to said proximal end of said needle on said suturing device.

49. The suturing device as recited in claim 30, wherein said needle carriage is disposed on one of said first and second jaw members.

50. The suturing device as recited in claim 49, wherein said one of said first and second jaw members comprises a lower jaw member which is stationary relative to the other of said first and second jaw members.

51. The suturing device as recited in claim 50, wherein said one of said first and second jaw members further comprises a jaw plate, said jaw plate including at least one needle guide for providing a track for said at least one needle to ride in, when said at least one needle travels between said distal and proximal positions.

52. The suturing device as recited in claim 51, wherein said one of said first and second jaw members comprises a removable end cap, for permitting installation of a new needle carriage.

53. The suturing device as recited in claim 50, wherein the other of said first and second jaw members comprises an upper jaw member which is movable relative to the lower jaw member, said upper jaw member including a needle catch having at least one slot thereon for capturing the distal end of the at least one needle when it has been actuated from said distal position to said proximal position.

54. The suturing device as recited in claim 50, wherein suture attached to said at least one needle is enclosed by a ferrule, and the other of said first and second jaw members comprises an upper jaw member which is movable relative to the lower jaw member, said upper jaw member including a ferrule catch having at least one slot thereon for capturing the ferrule enclosing the suture connected to the at least one needle.

55. The suturing device as recited in claim 30, wherein said at least one needle comprises two spaced needles.

56. A suturing device for use endoscopically, comprising:
a first jaw member,
a second jaw member, said first and second jaw members being disposed at a distal end of said suturing device, said second jaw member being movable relative to said first jaw member;
an actuator disposed at a proximal end of the suturing device, for actuating the first and second jaw members between a closed orientation, wherein distal ends of the jaw members are disposed in close proximity to one another, and an open orientation, wherein said distal jaw member ends are substantially spaced from one another;
at least one needle disposed on said first jaw member, said at least one needle being attached to suturing material and including a penetrating tip, said at least one needle and attached suturing material being movable between a retracted position and an extended position for passage through tissue grasped between said first and second jaw members; and
a catch apparatus disposed on said second jaw member, said catch apparatus including structure for capturing one of said at least one needle and said suturing material when said at least one needle is moved to said extended position.

57. The suturing device as recited in claim 56, wherein said at least one needle comprises two spaced needles.

58. The suturing device as recited in claim 56, wherein said catch apparatus includes at least one slot, corresponding to said at least one needle.

59. The suturing device as recited in claim 58, wherein said at least one slot captures said at least one needle.

60. The suturing device as recited in claim 58, wherein said at least one slot captures a ferrule disposed on said suturing material.

* * * * *

UNITED STATES PATENT AND TRADEMARK OFFICE
CERTIFICATE OF CORRECTION

PATENT NO. : 6,533,795 B1
DATED : March 18, 2003
INVENTOR(S) : Tran et al.

It is certified that error appears in the above-identified patent and that said Letters Patent is hereby corrected as shown below:

Column 2,
Line 43, after "a" change "tom" to -- torn --.

Column 4,
Line 51, after "a" change "tom" to -- torn --.

Column 11,
Line 8, after "the" change "tom" to -- torn --.
Line 43, after "is" change "sidably" to -- slidably --.

Column 12,
Line 55, after "the" change "tom" -- torn --.

Signed and Sealed this

Twenty-fifth Day of January, 2005

JON W. DUDAS
*Director of the United States Patent and Trademark Office*